United States Patent
Hincapie et al.

(10) Patent No.: US 10,632,226 B2
(45) Date of Patent: *Apr. 28, 2020

(54) POLYMER PARTICLES

(71) Applicant: Terumo Corporation, Tokyo (JP)

(72) Inventors: Gloria Hincapie, Aliso Viejo, CA (US);
Xinping Wu, Aliso Viejo, CA (US);
Yue Wu, Aliso Viejo, CA (US);
Gregory M. Cruise, Rancho Santa Margarita, CA (US)

(73) Assignee: Terumo Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/237,298

(22) Filed: Dec. 31, 2018

(65) Prior Publication Data

US 2019/0134257 A1   May 9, 2019

Related U.S. Application Data

(63) Continuation of application No. 15/719,241, filed on Sep. 28, 2017, now Pat. No. 10,201,632.

(Continued)

(51) Int. Cl.
*A61L 24/00* (2006.01)
*A61L 26/00* (2006.01)
(Continued)

(52) U.S. Cl.
CPC ...... *A61L 24/0015* (2013.01); *A61K 31/4745* (2013.01); *A61K 31/555* (2013.01); *A61K 47/6927* (2017.08); *A61L 24/0042* (2013.01); *A61L 24/06* (2013.01); *A61L 26/009* (2013.01); *A61L 26/0014* (2013.01); *A61L 26/0061* (2013.01); *A61L 31/048* (2013.01); *A61L 31/148* (2013.01); *C08F 220/56* (2013.01); *C08F 236/20* (2013.01);
(Continued)

(58) Field of Classification Search
CPC ............ A61K 47/6927; A61K 31/4745; A61K 31/555; A61L 24/0042; A61L 24/06; A61L 26/0014; A61L 26/0061; A61L 26/009; A61L 31/048; A61L 31/148; C08F 220/56; C08F 236/20
USPC ........................................................ 428/402
See application file for complete search history.

(56) References Cited

U.S. PATENT DOCUMENTS

| | | |
|---|---|---|
| 4,070,348 A | 1/1978 | Kraemer et al. |
| 4,157,323 A | 6/1979 | Yen et al. |

(Continued)

FOREIGN PATENT DOCUMENTS

| | | |
|---|---|---|
| CN | 103709323 A | 4/2014 |
| EP | 0240424 B1 | 5/1991 |

(Continued)

OTHER PUBLICATIONS

European Search Report and Search Opinion dated Jul. 10, 2017 for European Patent Application Serial No. 14859554.9.

(Continued)

*Primary Examiner* — Alexandre F Ferre
(74) *Attorney, Agent, or Firm* — K&L Gates LLP; Louis C. Cullman; Brian J. Novak

(57) ABSTRACT

Biodegradable, cross-linked polymer particle embolics and methods of making the same are described. The particle embolics can be used as embolization agents.

20 Claims, 5 Drawing Sheets

Related U.S. Application Data

(60) Provisional application No. 62/401,091, filed on Sep. 28, 2016, provisional application No. 62/428,990, filed on Dec. 1, 2016.

(51) Int. Cl.

| | | |
|---|---|---|
| *A61K 47/69* | (2017.01) | |
| *A61K 31/4745* | (2006.01) | |
| *A61K 31/555* | (2006.01) | |
| *A61L 24/06* | (2006.01) | |
| *C08F 220/56* | (2006.01) | |
| *A61L 31/04* | (2006.01) | |
| *A61L 31/14* | (2006.01) | |
| *C08F 236/20* | (2006.01) | |
| *A61B 17/12* | (2006.01) | |
| *A61B 17/00* | (2006.01) | |

(52) U.S. Cl.
CPC ... *A61B 17/12109* (2013.01); *A61B 17/12113* (2013.01); *A61B 17/12181* (2013.01); *A61B 2017/00004* (2013.01); *A61L 2300/204* (2013.01); *A61L 2300/224* (2013.01); *A61L 2400/06* (2013.01); *A61L 2430/36* (2013.01)

(56) References Cited

U.S. PATENT DOCUMENTS

| | | | |
|---|---|---|---|
| 4,925,677 A | 5/1990 | Feijen | |
| 5,417,982 A | 5/1995 | Modi | |
| 5,545,423 A | 8/1996 | Soon-Shiong et al. | |
| 5,635,215 A | 6/1997 | Boschetti et al. | |
| 5,648,100 A | 7/1997 | Boschetti et al. | |
| 5,662,935 A | 9/1997 | Motta | |
| 5,759,578 A | 6/1998 | Soon-Shiong et al. | |
| 5,879,709 A | 3/1999 | Soon-Shiong et al. | |
| 5,906,997 A | 5/1999 | Schwartz et al. | |
| 5,922,357 A | 7/1999 | Coombes et al. | |
| 6,087,450 A | 7/2000 | Breitbach et al. | |
| 6,218,440 B1 | 4/2001 | Kitagawa | |
| 6,248,363 B1 | 6/2001 | Yoshikawa et al. | |
| 6,306,922 B1 | 10/2001 | Hubbell et al. | |
| 6,309,669 B1 | 10/2001 | Setterstrom et al. | |
| 6,403,569 B1 | 6/2002 | Achterrath | |
| 6,548,081 B2 | 4/2003 | Sadozai et al. | |
| 6,555,138 B1 | 4/2003 | Karlsson et al. | |
| 6,569,463 B2 | 5/2003 | Patel et al. | |
| 6,689,374 B2 | 2/2004 | Chu et al. | |
| 6,790,456 B2 | 9/2004 | Vogel et al. | |
| 6,794,370 B2 | 9/2004 | Achterrath | |
| 6,923,988 B2 | 8/2005 | Patel et al. | |
| 6,946,146 B2 | 9/2005 | Muyle | |
| 7,070,809 B2 | 7/2006 | Goupil et al. | |
| 7,094,369 B2 | 8/2006 | Buiser et al. | |
| 7,144,588 B2 | 12/2006 | Oray et al. | |
| 7,153,572 B2 | 12/2006 | Cooper et al. | |
| 7,442,385 B2 | 10/2008 | Lewis et al. | |
| 7,449,236 B2 | 11/2008 | Lanphere et al. | |
| 7,462,366 B2 | 12/2008 | Lanphere et al. | |
| 7,588,780 B2 | 9/2009 | Buiser et al. | |
| 7,591,993 B2 | 9/2009 | Boschetti | |
| 7,670,592 B2 | 3/2010 | Boschetti | |
| 7,736,671 B2 | 6/2010 | DiCarlo et al. | |
| 7,776,240 B2 | 8/2010 | Chu et al. | |
| 7,794,755 B2 | 9/2010 | Figuly et al. | |
| 7,838,035 B2 | 11/2010 | Figuly | |
| 7,838,699 B2 | 11/2010 | Schwarz et al. | |
| 7,842,377 B2 | 11/2010 | Lanphere et al. | |
| 7,858,119 B1 | 12/2010 | Odidi et al. | |
| 7,887,846 B2 | 2/2011 | Figuly | |
| 7,897,179 B2 | 3/2011 | Muyle | |
| 7,951,402 B2 | 5/2011 | Lanphere et al. | |
| 8,062,673 B2 | 11/2011 | Figuly et al. | |
| 8,110,226 B2 | 2/2012 | Li | |
| 8,143,042 B2 | 3/2012 | Bettinger et al. | |
| 8,182,807 B2 | 5/2012 | Labhasetwar et al. | |
| 8,201,689 B2 | 6/2012 | Kaem | |
| 8,226,926 B2 | 7/2012 | Reb | |
| 8,252,302 B2 | 8/2012 | Macdonald | |
| 8,323,698 B2 | 12/2012 | Gu et al. | |
| 8,323,794 B2 | 12/2012 | Chu et al. | |
| 8,329,224 B2 | 12/2012 | Hall et al. | |
| 8,367,099 B2 | 2/2013 | Herweck et al. | |
| 8,383,758 B2 | 2/2013 | Papisov | |
| 8,426,481 B2 | 4/2013 | Hassleholm et al. | |
| 8,617,132 B2 | 12/2013 | Golzarian et al. | |
| 8,673,266 B2 | 3/2014 | Boschetti | |
| 8,691,791 B2 | 4/2014 | Lewis et al. | |
| 8,697,137 B2 | 4/2014 | Vogel et al. | |
| 8,709,384 B2 | 4/2014 | Reb | |
| 8,739,978 B2 | 6/2014 | Yoon et al. | |
| 8,741,351 B2 | 6/2014 | Vogel et al. | |
| 9,546,236 B2 * | 1/2017 | Cruise | C08F 220/56 |
| 9,803,043 B2 * | 10/2017 | Cruise | C08F 220/56 |
| 9,938,367 B2 * | 4/2018 | Cruise | C08F 220/56 |
| 10,118,980 B1 | 11/2018 | Plotkin et al. | |
| 10,144,793 B2 * | 12/2018 | Cruise | C08F 220/56 |
| 10,155,064 B2 | 12/2018 | Cruise et al. | |
| 10,201,632 B2 * | 2/2019 | Hincapie | A61K 47/6927 |
| 2002/0028243 A1 | 3/2002 | Masters | |
| 2002/0068089 A1 | 6/2002 | Vogel et al. | |
| 2002/0071855 A1 | 6/2002 | Sadozai et al. | |
| 2002/0197326 A1 | 12/2002 | Vogel et al. | |
| 2003/0078339 A1 | 4/2003 | Kiser et al. | |
| 2003/0183962 A1 | 10/2003 | Buiser et al. | |
| 2003/0206864 A1 | 11/2003 | Mangin | |
| 2004/0161466 A1 | 8/2004 | Lewis et al. | |
| 2005/0196702 A1 | 9/2005 | Bryant et al. | |
| 2005/0267556 A1 | 12/2005 | Shuros et al. | |
| 2006/0025560 A1 | 2/2006 | Inoue et al. | |
| 2006/0069168 A1 | 3/2006 | Tabata et al. | |
| 2006/0222596 A1 | 10/2006 | Askari et al. | |
| 2006/0240435 A1 | 10/2006 | Minoura et al. | |
| 2006/0251582 A1 | 11/2006 | Reb | |
| 2007/0035296 A1 | 2/2007 | Potapov et al. | |
| 2007/0213683 A1 | 9/2007 | Cassingham et al. | |
| 2007/0237741 A1 | 10/2007 | Figuly et al. | |
| 2007/0237742 A1 | 10/2007 | Figuly et al. | |
| 2007/0237830 A1 | 10/2007 | Figuly | |
| 2007/0237956 A1 | 10/2007 | Figuly et al. | |
| 2008/0033366 A1 | 2/2008 | Matson et al. | |
| 2008/0039890 A1 | 2/2008 | Matson et al. | |
| 2008/0102029 A1 | 5/2008 | Fritz et al. | |
| 2008/0113029 A1 | 5/2008 | Fritz et al. | |
| 2008/0220077 A1 | 9/2008 | Vogel et al. | |
| 2009/0029077 A1 | 1/2009 | Atanasoska et al. | |
| 2009/0092677 A1 | 4/2009 | Richard | |
| 2009/0117033 A1 | 5/2009 | O'Gara | |
| 2009/0164013 A1 | 6/2009 | Cruise et al. | |
| 2009/0246275 A1 | 10/2009 | O'Gara et al. | |
| 2009/0253809 A1 | 10/2009 | Gomurashvili et al. | |
| 2010/0028260 A1 | 2/2010 | Fritz et al. | |
| 2010/0040688 A1 | 2/2010 | Elbert et al. | |
| 2010/0057027 A1 | 3/2010 | Furno et al. | |
| 2010/0166876 A1 | 7/2010 | Lewis et al. | |
| 2010/0247667 A1 | 9/2010 | Ariga et al. | |
| 2010/0261646 A1 | 10/2010 | Lavik et al. | |
| 2011/0009327 A1 | 1/2011 | Hill et al. | |
| 2011/0009520 A1 | 1/2011 | Figuly et al. | |
| 2011/0033548 A1 | 2/2011 | Lai et al. | |
| 2011/0033608 A1 | 2/2011 | Figuly et al. | |
| 2011/0038936 A1 | 2/2011 | Griswold et al. | |
| 2011/0082427 A1 | 4/2011 | Golzarian et al. | |
| 2011/0091550 A1 | 4/2011 | Zhang et al. | |
| 2011/0152765 A1 | 6/2011 | Weber et al. | |
| 2011/0182998 A1 | 7/2011 | Reb et al. | |
| 2011/0212179 A1 | 9/2011 | Liu | |
| 2012/0129798 A1 | 5/2012 | Akala et al. | |
| 2012/0135170 A1 | 5/2012 | Meldal et al. | |
| 2012/0213831 A1 | 8/2012 | Vogel et al. | |
| 2012/0276151 A1 | 11/2012 | Lewis et al. | |
| 2012/0289995 A1 | 11/2012 | Constant et al. | |
| 2012/0302654 A1 | 11/2012 | Cruise et al. | |
| 2013/0052142 A1 | 2/2013 | Harder et al. | |

(56) References Cited

U.S. PATENT DOCUMENTS

| | | |
|---|---|---|
| 2013/0190795 A1 | 7/2013 | Matson et al. |
| 2013/0315838 A1 | 11/2013 | Reb et al. |
| 2013/0323306 A1 | 12/2013 | Weber |
| 2014/0162969 A1 | 6/2014 | Lewis et al. |
| 2014/0186601 A1 | 7/2014 | Chang et al. |
| 2015/0079328 A1 | 3/2015 | Cruise et al. |
| 2015/0079395 A1 | 3/2015 | Cruise et al. |
| 2015/0166696 A1 | 6/2015 | Plotkin et al. |
| 2015/0306227 A1 | 10/2015 | Cruise et al. |
| 2016/0279282 A1 | 9/2016 | Cruise et al. |
| 2016/0311990 A1 | 10/2016 | Cruise et al. |
| 2017/0081450 A1 | 3/2017 | Cruise et al. |
| 2018/0085487 A1 | 3/2018 | Cruise et al. |
| 2018/0085497 A1 | 3/2018 | Hincapie et al. |
| 2019/0031798 A1 | 1/2019 | Plotkin et al. |
| 2019/0062479 A1 | 2/2019 | Cruise et al. |
| 2019/0076571 A1 | 3/2019 | Cruise et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | H05-279416 A | 10/1993 |
| JP | 2003-245544 A | 9/2003 |
| JP | 2011-201031 A | 10/2011 |
| JP | 2011-245267 A | 12/2011 |
| JP | 2012-170773 A | 9/2012 |
| JP | 2012-187308 A | 10/2012 |
| JP | 2014-218439 A | 11/2014 |
| WO | 1995/019186 A2 | 7/1995 |
| WO | 2001/072281 A2 | 10/2001 |
| WO | 2002/015913 A1 | 2/2002 |
| WO | 2002/071994 A1 | 9/2002 |
| WO | 2003/094930 A1 | 11/2003 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/047095 A1 | 4/2008 |
| WO | 2008/057163 A2 | 5/2008 |
| WO | 2008/128580 A1 | 10/2008 |
| WO | 2008/136536 A1 | 11/2008 |
| WO | 2009/015281 A2 | 1/2009 |
| WO | 2009/040434 A1 | 4/2009 |
| WO | 2009/073193 A2 | 6/2009 |
| WO | 2009/130332 A1 | 10/2009 |
| WO | 2009/131982 A1 | 10/2009 |
| WO | 2010/063630 A2 | 6/2010 |
| WO | 2011/014722 A2 | 2/2011 |
| WO | 2011/029867 A1 | 3/2011 |
| WO | 2011/068455 A1 | 6/2011 |
| WO | 2012/073188 A1 | 6/2012 |
| WO | 2012/120138 A1 | 9/2012 |
| WO | 2012/121073 A1 | 9/2012 |
| WO | 2012/133737 A1 | 10/2012 |
| WO | 2012/145431 A2 | 10/2012 |
| WO | 2012/166594 A1 | 12/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |
| WO | 2015/042462 A1 | 3/2015 |
| WO | 2015/070094 A1 | 5/2015 |
| WO | 2016/154592 A1 | 9/2016 |
| WO | 2018/064389 A1 | 4/2018 |
| WO | 2018/064390 A1 | 4/2018 |

OTHER PUBLICATIONS

International Search Report and Written Opinion dated Dec. 20, 2017 for International Application No. PCT/US2017/054118 filed on Sep. 28, 2017.

International Search Report and Written Opinion dated Feb. 27, 2018 for International Application No. PCT/US2017/054113 filed on Sep. 28, 2017.

U.S. Appl. No. 16/258,313, filed Jan. 25, 2019.

U.S. Appl. No. 16/403,364, filed May 3, 2019.

Blinova et al., Poly(ethylene glycol) containing functionalized polymer membranes for carbon dioxide separation. Preprints—American Chemical Society, Division of Energy & Fuels, 59(1):433-434 (2014).

International Search Report and Written Opinion dated Dec. 24, 2014 for International Application No. PCT/US2014/056647 filed on Sep. 19, 2014.

International Search Report and Written Opinion dated Feb. 27, 2015 for International Application No. PCT/US2014/064680 filed on Nov. 7, 2014.

International Search Report and Written Opinion dated Dec. 24, 2014 for International Application No. PCT/US2014/056644 filed on Sep. 19, 2014.

Kamitani et al., Design of cell-surface-retained polymers for artificial ligand display. ChemBioChem, 10(2):230-233 (2009).

Supplementary European Search Report dated Apr. 19, 2017 for European Application No. 14845609.

Supplementary European Search Report dated Apr. 6, 2017 for European Application No. 14845676.7.

International Search Report and Written Opinion dated Jun. 2, 2016 for International Application No. PCT/US2016/024340 filed on Mar. 25, 2016.

Tarasyuk et al., Investigation into the influence of organic modifiers and ultradispersed hybrid fillers on the structure and properties of glass-ceramic coatings prepared by the sol-gel method. Glass Physics and Chemistry, vol. 32, No. 4, pp. 439-447 (2006).

\* cited by examiner

POLYMER PARTICLES

CROSS REFERENCE TO RELATED APPLICATIONS

This application is a continuation of U.S. patent application Ser. No. 15/719,241, filed Sep. 28, 2017, which claims the benefit of U.S. provisional patent application No. 62/401,091, filed Sep. 28, 2016, and U.S. provisional patent application No. 62/428,990, filed Dec. 1, 2016, the entire disclosures of which are incorporated herein by reference.

FIELD

Biodegradable polymer particles for the occlusion of vascular sites and cavities within the body, such as the embolization of tumors or arteriovenous malformations, are described.

SUMMARY

Described herein generally are biodegradable, crosslinked polymer particles. In some embodiments, the particles can have a spherical shape or be substantially spherical. Thus, the particles described herein can be referred to as microspheres or polymer spheres. These polymers can be used for/in embolization. The polymer particles can include and/or be formed of one or more monomers and a crosslinker susceptible to chemical hydrolysis or enzymatic action.

The biodegradable polymer particles described herein can be utilized for the occlusion of vascular sites, bodily lumen, and other cavities within the body. In some embodiments, the polymer particles can be used for such purposes as the embolization of tumors or arteriovenous malformations.

Polymer particles can comprise: at least one monomer and at least one crosslinker. In some embodiments, the polymer particles can be susceptible to degradation through chemical hydrolysis or enzymatic action. Particles as described herein can have various sizes depending on a particular use, but generally can have diameters between about 40 μm and about 1,200 μm or between about 75 μm and about 1,200 μm.

Methods of making a polymer particle as described herein are also described. These methods comprise: preparing a prepolymer solution including at least one monomer, at least one crosslinker susceptible to degradation through chemical hydrolysis or enzymatic action, and an initiator; dispersing the prepolymer solution in mineral oil; and forming the polymer particles via polymerization of the monomers.

Other methods to form polymer particles can include: reacting a prepolymer solution in an oil to form the polymer particles. The prepolymer solution can include at least one monomer comprising at least one functional group, at least one crosslinker susceptible to degradation through chemical hydrolysis or enzymatic action, and an initiator.

In one embodiment, the polymer particles can be prepared from monomers having a single functional group suitable to polymerization. Functional groups suitable to free radical polymerization, include but are not limited to, acrylate, acrylamide, methacrylate, and methacrylamide. Other polymerization methods including nucleophile/N-hydroxysuccinimide esters, nucleophile/halide, vinyl sulfone/acrylate or maleimide/acrylate, can be utilized. Selection of the monomers can be governed by the desired mechanical properties of the resulting particle and minimizing the biological effect of the degradation products.

In some embodiments, the monomer used can include an ionizable functional group that is basic (e.g. amines, derivatives thereof, or combinations thereof). A basic, amine group may be protonated at pH's less than the pKa of the amine, and deprotonated at pH's greater than the pKa of the amine. In other embodiments, the monomer can include an ionizable functional group that is acidic (e.g. carboxylic acids, sulfonic acids, phosphoric acids, derivatives thereof, or combinations thereof). The acid group may be deprotonated at pH's greater than the pKa of the acid, and protonated at pH's less than the pKa of the acid.

In one embodiment, the at least one crosslinker can include at least two functional groups suitable to polymerization and at least one linkage susceptible to breakage and/or cleavage. This breakage and/or cleavage can impart biodegradation to the polymer particle. Linkages susceptible to breakage in a physiological environment include those susceptible to hydrolysis, including esters, thioesters, carbamates, anhydrides, phosphoesters, peptides and carbonates. Multiple crosslinkers could be utilized to control the rate of degradation in a manner that is not possible with only one.

DRAWINGS

FIG. 1 illustrates grading scores for the samples included in Example 10. (5) no change in particle numbers, outlines, or quantity from the beginning of the experiment, (3) faint particle outline with a good number of particles still visible, (1) very few particles visible, and (0) no particles observed in the sample. Results for the comparison of different crosslinking agents are illustrated in FIG. 1. The results illustrate that degradation rate can be dependent on the structure of the crosslinker used.

DETAILED DESCRIPTION

Figure 1:
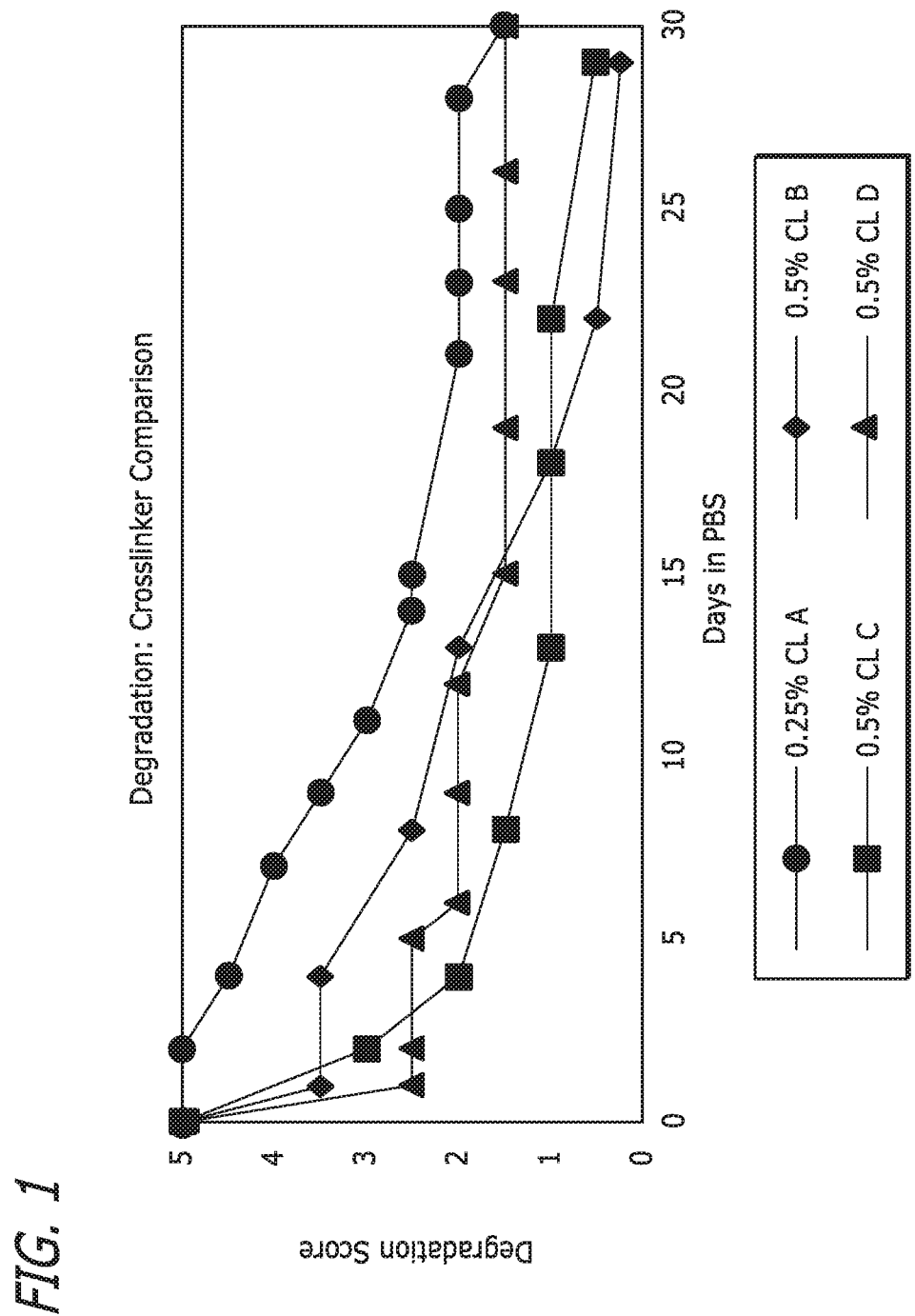

Described herein generally are particles made of polymer material. The polymer material can be a reaction product of one or more monomers and one or more crosslinkers. The monomers can include a singular functional group amenable to polymerization. In some embodiments, the polymer particles can be susceptible to hydrolysis or enzymatic action. The particles can be referred to herein as being microparticles, microspheres and the like. The particles can have a diameter of between about 40 μm and about 1,200 μm or between about 75 μm and about 1,200 μm. The particles can also be compressible and/or durable for ease of delivery through a medical device such as a needle or catheter. The particles can also be biodegradable once delivered.

The particles can be formed from a mixture such as a prepolymer solution. The prepolymer solution can comprise: (i) one or more monomers that contain a singular functional group amenable to polymerization and (ii) one or more crosslinkers. In some embodiments, a polymerization initiator may be utilized.

In some embodiments, if one of the monomer(s) and/or crosslinker(s) is a solid, a solvent can be utilized in the preparation of the particles for use as embolics. If liquid monomers and crosslinkers are utilized, a solvent may not be required, but may still be desired. In some embodiments, even when using liquid monomers and crosslinkers, a solvent may still be used. Solvents may include any liquid that can dissolve or substantially dissolve a monomer, monomer mixture, and/or a crosslinker. Any aqueous or organic solvent may be used that dissolves the desired monomer(s), crosslinker(s), and/or polymerization initiators. In one embodiment, the solvent can be water. In another embodiment, the solvent can be N,N-dimethylformamide, formamide, or dimethyl sulfoxide. In one embodiment, if an organic solvent is used, dimethyl sulfoxide may be used for dispersion. In other embodiments, if an organic solvent is used, an aqueous media may be used for dispersion. Additionally, solutes, e.g. sodium chloride, may be added to the solvent to increase the rate of polymerization. Solvent concentrations can be about 10% w/w, about 20% w/w, about 30% w/w, about 40% w/w, about 50% w/w, about 60% w/w, about 70% w/w, about 80% w/w, about 90% w/w, between about 20% w/w and about 80% w/w, between about 50% w/w and about 80% w/w, or between about 30% w/w and about 60% w/w of the solution.

Any type of crosslinking chemistry can be utilized to prepare the described polymer particles. In some embodiments, for example crosslinking chemistries such as, but not limited to nucleophile/N-hydroxysuccinimide esters, nucleophile/halide, vinyl sulfone/acrylate or maleimide/acrylate, or free radical polymerization can be used. In one example embodiment, free radical polymerization can be used. As such, monomers with a singular ethylenically unsaturated group, such as acrylate, acrylamide, methacrylate, methacrylamide, and vinyl, may be used when employing free radical polymerization.

Any amount of monomer can be used that allows for a desired particle. Monomer concentration in the solvent can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 40% w/w and about 60% w/w, between about 50% w/w and about 60% w/w, between about 10% w/w and about 50% w/w, between about 20% w/w and about 60% w/w, or between about 40% w/w and about 60% w/w.

Monomers can be selected based on imparting desired chemical and/or mechanical properties to the polymer particle or particle embolic. If desired, uncharged, reactive moieties can be introduced into the particle embolic. For example, hydroxyl groups can be introduced into the particle embolic with the addition of 2-hydroxyethyl acrylate, 2-hydroxymethacrylate, glycerol monomethacrylate, derivatives thereof, or combinations thereof. Alternatively, uncharged, relatively unreactive moieties can be introduced into the particle embolic. For example, acrylamide, methacrylamide, methyl methacrylate, dimethyl acrylamide, derivatives thereof, or combinations thereof can be added.

In some embodiments, the monomers can be glycerol monomethacrylate and dimethylacrylamide. The concentration of glycerol monomethacrylate in the solvent can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 5% w/w and about 50% w/w, between about 10% w/w and about 30% w/w, between about 15% w/w and about 25.

The concentration of dimethylacrylamide in the solvent can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 1% w/w and about 10% w/w, between about 1% w/w and about 5% w/w, between about 5% w/w and about 10% w/w.

In one embodiment, polymer particles can be prepared from monomers having a single functional group suitable for polymerization. Functional groups can include those suitable to free radical polymerization, such as acrylate, acrylamide, methacrylate, and methacrylamide. Other polymerization schemes can include, but are not limited to, nucleophile/N-hydroxysuccinimide esters, nucleophile/halide, vinyl sulfone/acrylate or maleimide/acrylate. Selection of the monomers is governed by the desired mechanical properties of the resulting particle and minimizing the biological effects of degradation products.

In some embodiments, the monomer can additionally contain an ionizable functional group that is basic (e.g. amines, derivatives thereof, or combinations thereof). The amine group may be protonated at pH's less than the pKa of the amine, and deprotonated at pH's greater than the pKa of the amine. In other embodiments, the monomer additionally contains an ionizable functional group that is acidic (e.g. carboxylic acids, sulfonic acids, phosphoric acids, derivatives thereof, or combinations thereof). The acid group may be deprotonated at pH's greater than the pKa of the acid, and protonated at pH's less than the pKa of the acid.

If the binding of positively charged drugs is desired, monomers with negatively charged moieties, e.g. carboxylic acids, or other acidic moieties can be polymerized into the particle embolic. Acidic, ionizable, ethylenically unsaturated monomers can include, but are not limited to, acrylic acid, methacrylic acid, 3-sulfopropyl acrylate, 3-sulfopropyl methacrylate, derivatives thereof, combinations thereof, and salts thereof. On the other hand, if the binding of negatively charged drugs is desired, monomers with positively charged moieties, e.g. amines, or other basic moieties can be included in the particle. Basic, ionizable, ethylenically unsaturated monomers can include, but are not limited to, 2-aminoethyl methacrylate, 3-aminopropyl methacrylate, derivatives thereof, combinations thereof, and salts thereof.

In some embodiments, the negatively charged monomers can be 3-sulfopropyl acrylate, potassium salt and 3-sulfopropyl acrylate. The concentration of 3-sulfopropyl acrylate, potassium salt and 3-sulfopropyl acrylate in the solvent can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 10% w/w and about 50% w/w, between about 20% w/w and about 40% w/w, between about 30% w/w and about 40% w/w.

An additional factor in monomer selection can be the desire for degradation products of the particle embolic to elicit a negligible response from the host. In other embodiments, there can be desire for degradation products of the particles to elicit substantially no response from the host.

A crosslinker can include two or more polymerizable groups, can join monomer chains together, and permit the formation of solid particles. Biodegradation can be imparted to the particle embolic by utilizing a crosslinker with linkages susceptible to degradation in a physiological environment. Over time in vivo, linkages can break and the polymer chains may no longer be bound together. The judicious selection of monomers can permit the formation of water-soluble degradation products that diffuse away and are cleared by the host. Linkages susceptible to hydrolysis, such as esters, thioester, carbamates, anhydrides, phosphoesters, peptides, and carbonates can be used in biodegradable products.

In one embodiment, the one or more crosslinker can include at least two functional groups suitable to polymerization and at least one linkage susceptible to breakage and/or cleavage. This breakage and/or cleavage can impart biodegradation to the polymer particle. Linkages susceptible to breakage in a physiological environment include those susceptible to hydrolysis, including esters, thioesters, carbamates, anhydrides, phosphoesters, peptides and carbonates. Multiple crosslinkers could be utilized to control the rate of degradation in a manner that is not possible with only one.

In other embodiments, the polymers can include a second crosslinker including a second linkage selected from an ester, a thioester, a carbonate, a carbamate, a peptide cleavable by matrix metalloproteinases, a peptide cleavable by matrix collagenases, a peptide cleavable by matrix elastases, and a peptide cleavable by matrix cathepsins.

In still other embodiments, the polymers can include a third, fourth, fifth or more crosslinkers each including the same or a different linkage.

Concentrations of the crosslinkers in the solvent can be about 5% w/w, about 10% w/w, about 15% w/w, about 20% w/w, about 25% w/w, about 30% w/w, about 35% w/w, between about 20% w/w and about 30% w/w, between about 10% w/w and about 60% w/w, or between about 20% w/w and about 50% w/w. A skilled artisan understands how to calculate final concentrations based on the amount in solvent already discussed.

In other embodiments, concentrations of the crosslinkers in the solvent can be about 0.05% w/w, about 0.1% w/w, about 0.5% w/w, about 1.0% w/w, about 2.0% w/w, about 3.0% w/w, about 4.0% w/w, between about 0.1% w/w and about 4.0% w/w, between about 0.5% w/w and about 2% w/w, or between about 1% w/w and about 1.5% w/w. A skilled artisan understands how to calculate final concentrations based on the amount in solvent already discussed.

In one embodiment, crosslinkers can have a structure

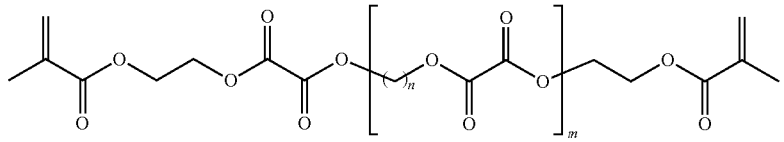

wherein m is 0, 1, 2, 3, 4, 5, 6, 7, 8, 9, 10, 11, 12, 13, 14, or 15 and/or n is 1, 2, 3, 4, 5, 6, 7, 8, 9, 10, 11, 12, 13, 14, 15, 16, 17, or 18. In one embodiment, m is 1 and n is 3.

In one embodiment, crosslinkers can have a structure

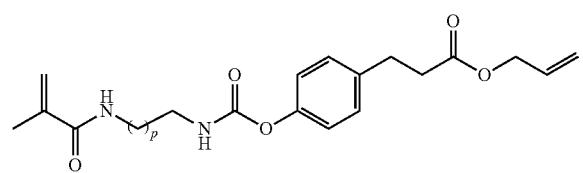

wherein p is 0, 1, 2, 3, 4, 5, 6, 7, 8, 9, 10, 11, 12, 13, 14, or 15. In one embodiment, p is 4. In another embodiment, p is 1.

In one embodiment, crosslinkers can have a structure

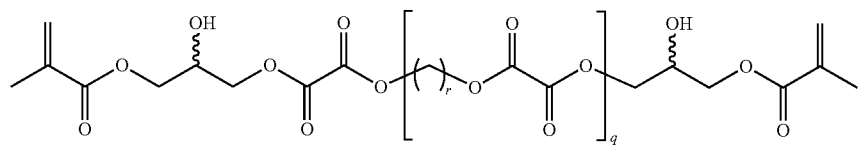

wherein q is 0, 1, 2, 3, 4, 5, 6, 7, 8, 9, 10, 11, 12, 13, 14, or 15 and/or r is 0, 1, 2, 3, 4, 5, 6, 7, 8, 9, 10, 11, 12, 13, 14, or 15. In one embodiment, q is 0 and r is 0.

In one embodiment, crosslinkers can have a structure

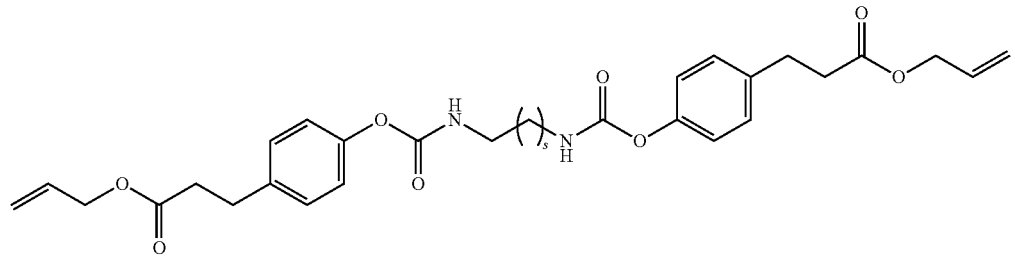

wherein s is 0, 1, 2, 3, 4, 5, 6, 7, 8, 9, 10, 11, 12, 13, 14, or 15. In one embodiment, s is 2.

In one embodiment, crosslinkers can have a structure

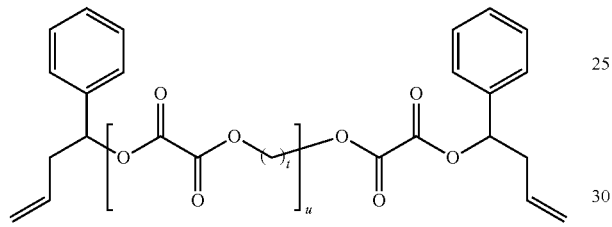

wherein t is 0, 1, 2, 3, 4, 5, 6, 7, 8, 9, 10, 11, 12, 13, 14, or 15 and/or u is 0, 1, 2, 3, 4, 5, 6, 7, 8, 9, 10, 11, 12, 13, 14, or 15. In one embodiment, t is 0 and u is 0.

In one embodiment, crosslinkers can have a structure

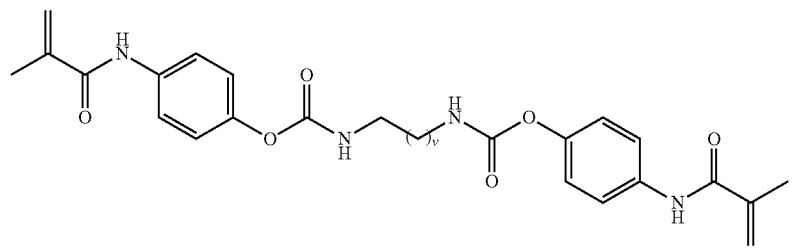

wherein v is 0, 1, 2, 3, 4, 5, 6, 7, 8, 9, 10, 11, 12, 13, 14, or 15. In one embodiment, v is 5. In another embodiment, v is 1.

In one embodiment, crosslinkers can have a structure

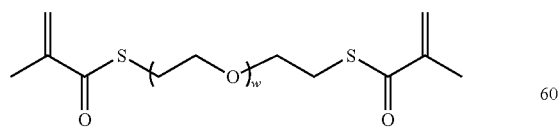

wherein w is 0, 1, 2, 3, 4, 5, 6, 7, 8, 9, 10, 11, 12, 13, 14, or 15. In one embodiment, w is 5.

In one embodiment, crosslinkers can have a structure

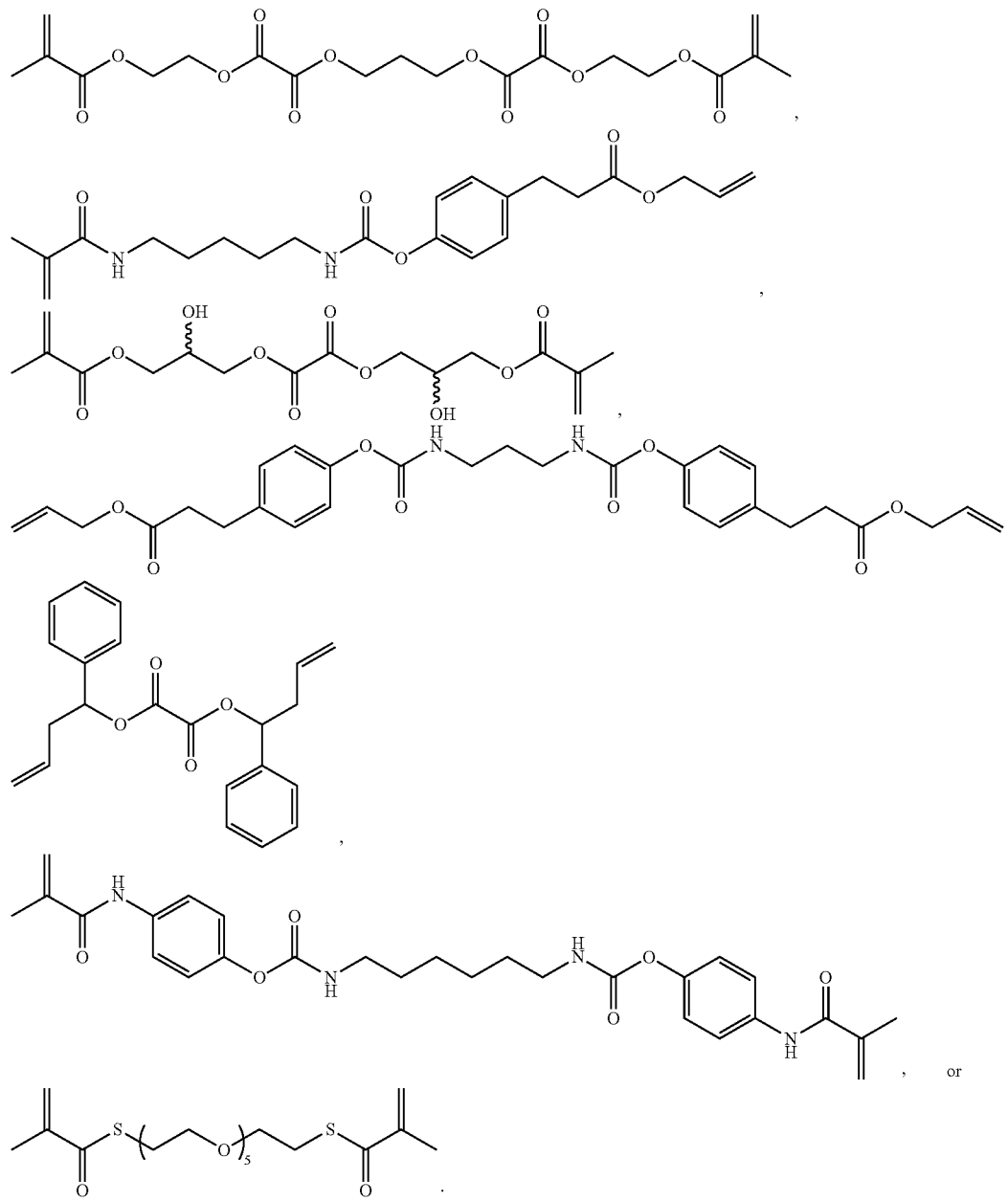

In some embodiments, a crosslinker can be a tetra ester, a tetra-thiol ester or a dithiol ester. In other embodiments, the crosslinker can be a carbonate crosslinker. A glycidyl based crosslinker may be bis-glycidyl amino alcohol.

The prepolymer solution can be polymerized by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the prepolymer solution. The free radical polymerization of the monomers) and crosslinker(s) can require an initiator to start the reaction. In one embodiment, the cross-linking method utilizes azobisisobutyronitrile (AIBN) or another water soluble AIBN derivative (2,2'-azobis(2-methylpropionamidine) dihydrochloride). Other cross-linking agents can include N,N,N',N'-tetramethyethylenediamine, ammonium persulfate, benzoyl peroxides, and combinations thereof, including azobisisobutyronitriles. In one embodiment, the initiator is AIBN at a concentration of about 1% w/w to about 5% w/w.

Polymer particles can be produced or formed by methods including: reacting a prepolymer solution including at least one monomer including at least one functional group, at least one crosslinker susceptible to degradation, and an initiator in an oil.

The prepolymer solution can be prepared by dissolving the monomer(s), crosslinker(s), and optionally initiator(s) in the solvent. The particle embolics can be prepared by emulsion polymerization. A non-solvent for the monomer solution, typically mineral oil, is sonicated to remove any entrapped oxygen. The mineral oil and a surfactant are added to the reaction vessel. An overhead stirrer is placed in the reaction vessel. The reaction vessel is then sealed, degassed under vacuum, and sparged with an inert gas such as argon.

In another embodiment, the particles are prepared by emulsion polymerization by dissolving the monomer(s), crosslinker(s), and initiator(s) in the solvent. A non-solvent for the monomer solution, typically mineral oil when the monomer solvent is N,N-dimethylformamide, formamide, or dimethyl sulfoxide, is added to the reaction vessel with a surfactant. An overhead stirrer is placed in the reaction vessel. The reaction vessel is then sealed and sparged with argon while mixing to remove any entrapped oxygen. The monomer solution is added to the reaction vessel, where stirring suspends droplets of the polymerization solution in the mineral oil. The polymerization is allowed to proceed overnight at room temperature.

The rate of stirring can affect particle size, with faster stirring producing smaller particles. Stirring rates can be about 100 rpm, about 200 rpm, about 300 rpm, about 400 rpm, about 500 rpm, about 600 rpm, about 700 rpm, about 800 rpm, about 900 rpm, about 1,000 rpm, about 1,100 rpm, about 1,200 rpm, about 1,300 rpm, between about 200 rpm and about 1,200 rpm, between about 400 rpm and about 1,000 rpm, at least about 100 rpm, at least about 200 rpm, at most about 1,300 rpm, or at most about 1,200 rpm to produce particles with desired diameters.

The polymer particles described herein can have a generally or substantially spherical shape. The substantially spherical or spherical particles can have diameters of about 10 µm, about 20 µm, about 30 µm, about 40 µm, about 50 µm, about 60 µm, about 75 µm, about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, between about 50 µm and about 1,500 µm, between about 100 µm and about 1,000 µm, between about 75 µm and about 1,200 µm, at least about 50 µm, at least about 80 µm, at most about 1,500 µm, or at most about 1,200 µm. In some embodiments, the diameter can be between about 40 µm and about 1,200 µm, between about 40 µm and about 60 µm, between about 10 µm and about 50 µm, or between about 75 µm and about 1,200 µm.

The polymer particles can retain their diameters even after injection through a catheter or other delivery device. In other words, the polymer particles may not fall apart or otherwise fracture during delivery. In some embodiments, the polymer particles can retain about 99%, about 98%, about 97%, about 96%, about 95%, about 90%, greater than about 99%, greater than about 98%, greater than about 97%, greater than about 96%, greater than about 95%, greater than about 90%, between about 90% and about 100% of their diameter after delivery.

The polymer particles can also have a characteristic circularity or have a relative shape that is substantially circular. This characteristic describes or defines the form of a region on the basis of its circularity. Polymer particles as described herein can have a fraction of circularity of about 0.8, 0.9, 0.95, 0.96, 0.97, 0.98, 0.99, greater than about 0.8, greater than about 0.9, or greater than about 0.95. In one embodiment, the circularity of the polymer particles is greater than about 0.9.

The polymer particles can retain their circularity even after injection through a catheter or other delivery device. In some embodiments, the polymer particles can retain about 99%, about 98%, about 97%, about 96%, about 95%, about 90%, greater than about 99%, greater than about 98%, greater than about 97%, greater than about 96%, greater than about 95%, greater than about 90%, between about 90% and about 100% of their circularity after delivery.

Polymerization can be allowed to proceed as long as necessary to produce particles with desired resiliency. Polymerization can be allowed to proceed for about 1 hr, 2 hr, 3 hr, 4 hr, 5 hr, 6 hr, 7 hr, 8 hr, 9 hr, 10 hr, 11 hr, 12 hr, 18 hr, 24 hr, 48 hr, 72 hr, 96 hr, between about 1 hr and about 12 hr, between about 1 hr and about 6 hr, between about 4 hr and about 12 hr, between about 6 hr and about 24 hr, between about 1 hr and about 96 hr, between about 12 hr and about 72 hr, or at least about 6 hours.

Polymerization can be run at a temperature to produce particles with desired resiliency and/or reaction time. Polymerization can be run at a temperature of about 10° C., about 20° C., about 30° C., about 40° C., about 50° C., about 60° C., about 70° C., about 80° C., about 90° C., about 100° C., between about 10° C. and about 100° C., between about 10° C. and about 30° C., at least about 20° C., at most about 100° C., or at most room temperature. In one embodiment, polymerization occurs at room temperature.

After the polymerization is complete, the polymer particles are washed to remove any solute, mineral oil, unreacted monomer(s), and/or unbound oligomers. Any solvent may be utilized, but care should be taken if aqueous solutions are used to wash particles with linkages susceptible to hydrolysis. Washing solutions can include, but are not limited to acetone, alcohols, water and a surfactant, water, saline, buffered saline, and saline and a surfactant.

Optionally, the washed polymer particles can then be dyed to permit visualization before injection into a microcatheter. A dye bath can be made by dissolving sodium carbonate and the desired dye in water. Particle embolics are added to the dye bath and stirred. After the dying process, any unbound dye is removed through washing. After dying and washing, the particles can be packaged into vials or syringes, and sterilized.

After the preparation of the particle embolics, they can be optionally dyed to permit visualization during preparation by the physician. Any of the dyes from the family of reactive dyes which bond covalently to the particle embolics can be used. Dyes can include, but are not limited to, reactive blue 21, reactive orange 78, reactive yellow 15, reactive blue No. 19, reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, reactive blue No. 19, C.I. reactive blue 21, any of the color additives that are approved for use by the FDA part 73, subpart D, or any dye that will irreversibly bond to the polymer matrix of the particle embolic.

If the herein described polymer particle or microsphere does not adequately bind any of the reactive dyes described above, a monomer containing an amine can be added to the monomer solution in an amount to achieve the desired coloration. Examples of suitable amine containing monomers include aminopropyl methacrylate, aminoethyl methacrylate, aminopropyl acrylate, aminoethyl acrylate, derivatives thereof, combinations thereof, and salts thereof. Concentrations of the amine containing monomers in the final product can be less than or equal to about 1% w/w.

In another embodiment, monofunctional reactive dyes, such as monochlorotriazine dyes and monovinylsulfone dyes, which contain only one reactive center can be irreversibly reacted to a monomer which contains a nucleophilic functional group to form a polymerizable dye monomer. Monofunctional reactive dyes that can be utilized to synthesize dye monomers can include, but are not limited to, C.I. reactive orange 78, C.I. reactive yellow 15, C.I., reactive blue No. 19, and/or C.I. reactive red 180. Monomers can include, but are not limited to, 2-hydroxyethyl methacrylate, 2-aminoethyl methacrylate, and 3-aminopropyl methacrylate. The synthesis of dye monomers is generally carried out under alkaline conditions with elevated temperature. The dye monomers can be separated from the unreacted monomers and dyes using column chromatography. The dye monomers can be added into the prepolymer solution in various combinations and ratios so that after polymerization the microspheres are colored without additional dyeing procedures.

The particles described herein can be sterilized without substantially degrading the polymer. After sterilization, at least about 50%, about 60%, about 70%, about 80%, about 90%, about 95%, about 99%, or about 100% of the polymer can remain intact. In one embodiment, the sterilization method can be autoclaving and can be utilized before administration.

The final polymer particle preparation can be delivered to the site to be embolized via a catheter, microcatheter, needle, or other similar delivery device. A radiopaque contrast agent can be thoroughly mixed with the particle preparation in a syringe and injected through a catheter until blood flow is determined to be occluded from the site by interventional imaging techniques.

In some embodiments, it may be desirable for the particles to degrade over time. In other words, the particles can be degradable and/or biodegradable. In such embodiments, the particles can degrade to less than about 40%, about 30% about 20%, about 10%, about 5% or about 1% intact after about 2 days, 3 days, 4 days, 5 days, 6 days, 7 days, 8 days, 9 days, 10 days, about 1 week, about 2 weeks, about 1 month, about 2 months, about 6 months, about 9 months, about a year, about 2 years, about 5 years, or about 10 years. In one embodiment, the particles can be substantially degraded in less than about 1 month. In another embodiment, the particles can be substantially degraded in less than about 6 months. In some embodiments, the particles can be substantially degraded within about one week. In other embodiments, the particles can be substantially degraded within about six months. In some embodiments, the degradation can occur after implantation. In other embodiments, the particles can be substantially degraded within about one week of implantation. In other embodiments, the particles can be substantially degraded within about one week of implantation.

In some embodiments, degradability can be accelerated with an appropriate and/or adequate enzyme. In some embodiments, the polymer particles can be injected along with an enzyme that can accelerate the degradation of the particles. In other embodiments, an enzyme can be delivered to the site of the implanted particles at a remote time and accelerate degradation at that time.

In some embodiments, the greater the percentage of a crosslinker in the final polymer particles, the longer degradation takes. Additionally, the larger the particle diameter, the longer the degradation. Thus, the particles with the longest degradation time are those that have the largest concentration of crosslinker and the largest diameter. These two properties can be varied to tailor degradation time as needed.

The polymer particles described herein can be compressible yet durable enough not to break apart or fragment. Substantially no change in circularity or diameter of particles occurs during delivery through a microcatheter. In other words, after delivery through a microcatheter, the polymer particles described herein remain greater than about 60%, about 70%, about 80%, about 90%, about 95%, about 99%, or about 100% intact after delivery.

Further, in some embodiments, the particles can stick to the tissue and/or remain in place through friction with the tissues. In other embodiments, the particles can act as a plug in a vessel held in place by the flow and pressure of the blood itself. In still other embodiments, the particles can be cohesive enough to stick to one another to aid in agglomerating particles at a particular site of action.

Polymer particles described can be delivered through a microcatheter or other appropriate delivery device to a remote tissue or can be injected through a needle to local tissues. The polymer particles can be used for occlusion of vascular sites and cavities within the body.

In some embodiments, the polymer particles can be configured for embolization of tumors (e.g., hypervascularized tumors) or arteriovenous malformations. In some embodiments, a patient can be selected that exhibits a hypervascularized tumor and/or an arteriovenous malformation. A microcatheter can be navigated to the location of the tumor or malformation. Polymer particles as described herein can be injected into that site to stabilize it thereby treating the patient's condition.

In some embodiments, the polymer particles are bare. In other embodiments, the polymer particles can be loaded with a pharmaceutical agent. A pharmaceutical agent can include, but is not limited to, irinotecan, doxorubicin, epirubicin, idarubicin, or a combination thereof. The loading of the pharmaceutical agent into the polymer particle can occur onsite or offsite. The concentration of pharmaceutical agent can be determined by one of ordinary skill in the art. In some embodiments, the concentration of pharmaceutical agent can be 0-10% w/w, 10% w/w-20% w/w, 20% w/w-30% w/w, 30% w/w-40% w/w, 40% w/w-50% w/w, 50% w/w-60% w/w, 60% w/w-70% w/w, 70% w/w-80% w/w, 80% w/w-90% w/w, or 90% w/w-100% w/w. In some embodiments, a 1 mL microsphere sample can be loaded with 37.5 mg doxorubicin eluted 24.5 mg (65%) over the first day. In other embodiments, a 1 mL microsphere sample can be loaded with 50 mg irinotecan eluted over 45 mg (95%) over the first day.

In some embodiments, the pharmaceutical drug can be about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100%, at least about 5%, at least about 10%, at least about 15%, at least about 20%, at least about 25%, at least about 30%, at least about 35%, at least about 40%, at least about 45%, at least about 50%, at least about 60%, at least about 65%, at least about 70%, at least about 75%, at least about 80%, at least about 85%, at least about 90%, at least about 95%, at least about 100%, between about 0-10%, between about 5%-15%, between about 10%-20%, between about 15%-25%, between about 20%-30%, between about 25%-35%, between about 30%-40%, between about 35%-45%, between about 40%-50%, between about 45%-55%, between about 50%-60%, between about 55%-65%, between about 60%-70%, between about 65%-75%, between about 70%-80%, between about 75%-85%, between about 80%-90%, between about 85%-95%, or between about 90%-100% eluted over the first day. In some embodiments, this elution is after implantation.

In some embodiments, the pharmaceutical agent can have its highest systemic concentration at about 1 hr, about 2 hrs, about 3 hrs, about 4 hrs, about 5 hrs, about 6 hrs, about 7 hrs, about 8 hrs, about 9 hrs, about 10 hrs, about 11 hrs, about 12 hrs, about 13 hrs, about 14 hrs, about 15 hrs, about 16 hrs, about 17 hrs, about 18 hrs, about 19, hrs, about 20 hrs, about 21 hrs, about 22 hrs, about 23 hrs, about 24 hrs, at least about 1 hr, at least about 2 hrs, at least about 3 hrs, at least about 4 hrs, at least about 5 hrs, at least about 6 hrs, at least about 7 hrs, at least about 8 hrs, at least about 9 hrs, at least about 10 hrs, at least about 11 hrs, at least about 12 hrs, at least about 13 hrs, at least about 14 hrs, at least about 15 hrs, at least about 16 hrs, at least about 17 hrs, at least about 18 hrs, at least about 19, at least about 20 hrs, at least about 21 hrs, at least about 22 hrs, at least about 23 hrs, at least about 24 hrs, more than about 1 hr, more than about 2 hrs, more than about 3 hrs, more than about 4 hrs, more than about 5 hrs, more than about 6 hrs, more than about 7 hrs, more than about 8 hrs, more than about 9 hrs, more than about 10 hrs, more than about 11 hrs, more than about 12 hrs, more than about 13 hrs, more than about 14 hrs, more than about 15 hrs, more than about 16 hrs, more than about 17 hrs, more than about 18 hrs, more than about 19, more than about 20 hrs, more than about 21 hrs, more than about 22 hrs, more than about 23 hrs, or more than about 24 hrs after delivery.

EXAMPLES

Example 1

Biodegradable Crosslinker

Synthesis of 2-(methacryloxy)ethyl oxalyl monochloride, 3: An oven-dried 100 mL three-neck round bottom flask was purged under argon. The flask was fitted with a stir bar and an addition funnel. To the flask was added oxalyl chloride (1, 20 g, 158 mmol) and anhydrous dichloromethane (DCM) (15 mL) sequentially. To the addition funnel was added 2-hydroxyethyl methacrylate (HEMA) (2, 16 g, 123 mmol). The flask was cooled in an ice bath and HEMA was added dropwise to the reaction. After the addition was finished, the reaction was left stirring in the ice bath for 1 hour. The flask was pulled out of the ice bath and stirring was continued for 1 hour. To work up, removed the DCM and oxalyl chloride on a rotary evaporator. Avoid moisture from here on. The product is a greenish liquid. It does not move on a silica TLC plate and has strong UV absorption.

Synthesis of 4: An oven-dried 50 mL three-neck round bottom flask was purged under argon. The, 2-(methacryloxy) ethyl oxalyl monochloride (3, 12 g, 54.4 mmol) and anhydrous DCM (25.4 mL) were added to the reaction flask. Pyridine (5.08 g, 64.2 mmol) and 1,3-propanediol (1.88 g, 24.7 mmol) were then sequentially added to the flask. To work up, began with filtering off the white precipitate. The filtrate was then washed with 5% citric acid (50 mL×2). The DCM fraction was then washed with saturated sodium chloride (NaCl) (50 mL) and dried over sodium sulfate ($Na_2SO_4$). The solvent was removed under reduced pressure to give the crude product as a thick yellowish liquid. The product was obtained after a flash column separation (normal phase, ethyl acetate (EtOAc)/hexanes) as a clear liquid.

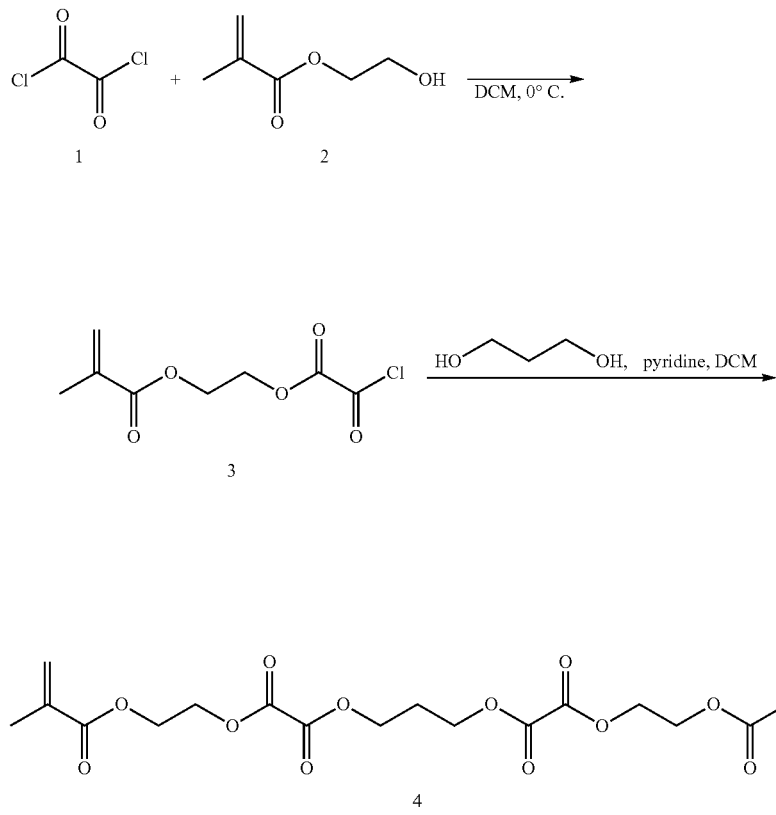

Example 2

Biodegradable Crosslinker

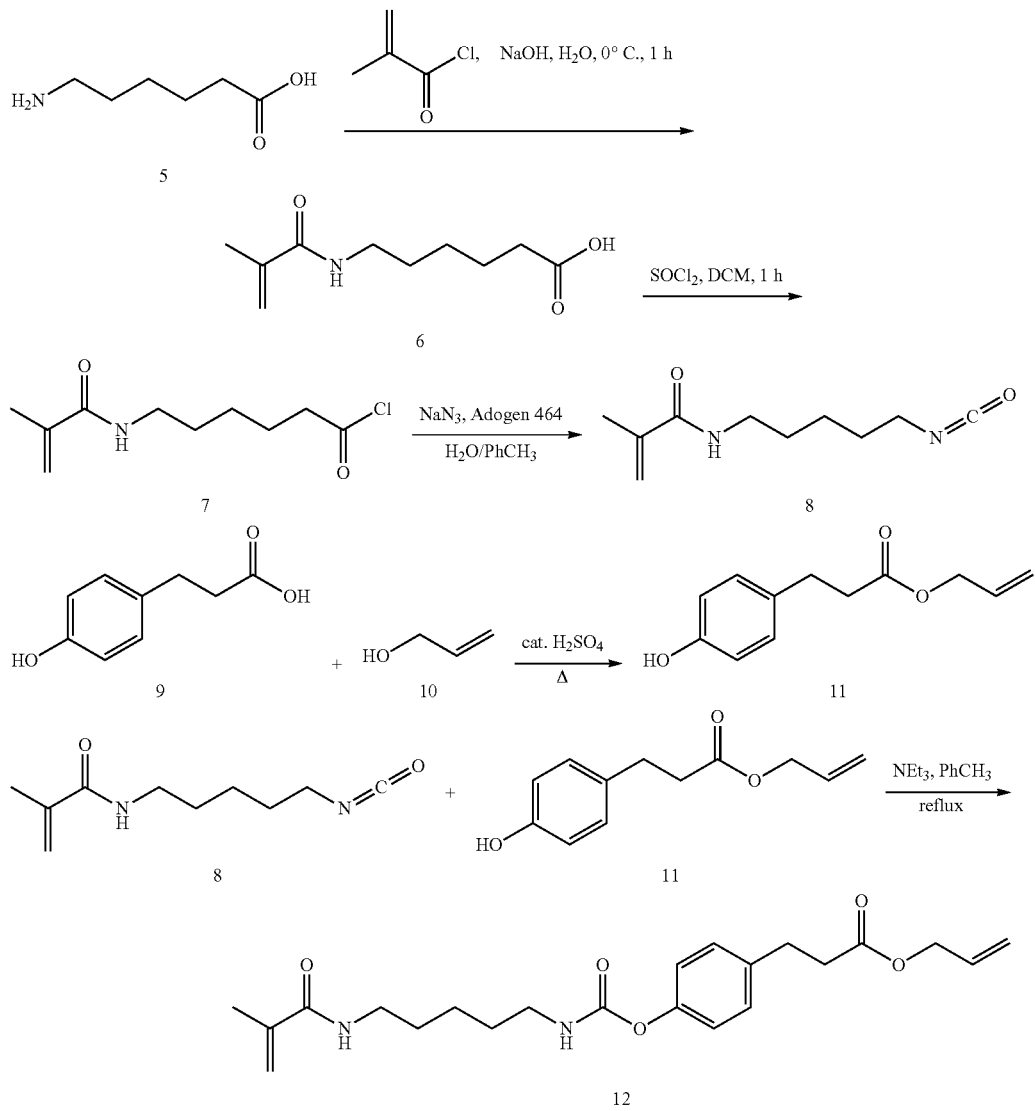

Synthesis of 6-(methacryloylamino)hexanoic acid, 6: In a 50 mL round bottom flask, 6-aminohexanoic acid (5, 8.45 g, 64.6 mmol) and sodium hydroxide (2.6 g, 65 mmol) were dissolved in distilled water (13 mL). The flask was cooled in an ice bath. To this solution was added methacryloyl chloride (6.26 mL, 64 mmol) dropwise and then stirred for two hours. To work up, washed the reaction with DOM (12.5 mL). The aqueous fraction was kept and the pH of the aqueous layer was adjusted to 2.0 with 1 M hydrochloric acid. The aqueous layer was extracted with EtOAc (30 mL×3). The organic fraction was combined and dried over $Na_2SO_4$. The solvent was removed under reduced pressure. The crude product was crystallized with EtOAc and hexanes to give the product as clear crystals (4.65 g, 36.5%).

Synthesis of 6-[(2-methyl-1-oxo-2-propen-1-yl)amino] hexanoyl chloride, 7: A three-neck round bottom flask was purged under argon. Then, 6-(methacryloylamino)hexanoic acid (6, 2.5 g, 12.6 mmol) and DCM (50 mL) were added to the flask. Then, thionyl chloride (4.50 g, 37.8 mmol) was added dropwise to the solution with stirring. The mixture was stirred for one hour. The solvent, thionyl chloride, and the byproduct were removed under reduced pressure to yield the product as a yellowish liquid.

Synthesis of N-(5-isocyanatopentyl)-2-methyl-2-propenamide, 8: A 100 mL round bottom flask fitted with a stir bar was purged under argon. To this flask was added sodium azide (0.774 g, 11.91 mmol), Adogen 464 (0.011 mL), and distilled water (25.1 mL) sequentially. The flask was cooled in an ice bath. To this aqueous solution was added toluene (25.1 mL) and 6-[(2-methyl-1-oxo-2-propen-1-yl)amino] hexanoyl chloride (7, 2.47 g, 11.3 mmol) sequentially. The mixture was stirred for 45 minutes and the aqueous layer was removed thereafter. The organic fraction was washed with distilled water (10 mL). The organic fraction was then dried over $Na_2SO_4$ and decolorized with charcoal. The $Na_2SO_4$ and charcoal were removed by filtration. The solvent was removed under reduced pressure to yield the product as a clear liquid (0.73 g).

Synthesis of allyl 3-(4-hydroxyphenyl)propionate, 11: To a 500 mL three-neck round bottom flask fitted with a stir bar was added 3-(4-hydroxyphenyl)propionic acid (9, 50 g, 0.3 mol) and allyl alcohol (10, 204 mL, 3 mol). To this mixture was added sulfuric acid (0.6 g, 6 mmol). The reaction was stirred at 95° C. overnight. The contents were cooled to room temperature and poured over distilled water (200 mL). The aqueous phase was extracted with dichloromethane (150 mL). The organic fraction was subsequently washed with distilled water (200 mL), saturated sodium bicarbonate (NaHCO$_3$) solution (200 mL, followed by 150 mL), and brine (200 mL). The organic fraction was dried over magnesium sulfate (MgSO$_4$) and the solvent was removed on a rotary evaporator. The crude product was decolorized with charcoal and stabilized with phenothiazine (28 mg). The crude product was further purified with flash chromatography (normal phase, hexanes/EtOAc) to yield the product as an oily liquid (43.8 g, 70.8%).

Synthesis of Carbamate Crosslinker, 12: To an oven-dried three-neck round bottom flask fitted with a stir bar was added phenothiazine (0.7 mg), N-(5-isocyanatopentyl)-2-methyl-2-propenamide (8, 730 mg, 4.31 mmol), toluene (5 mL), and triethylamine (600 µL) to the flask. A solution of allyl 3-(4-hydroxyphenyl)propionate (11, 740 mg, 3.59 mmol) in toluene (6 mL) was added. The solution was placed in an oil bath and refluxed overnight. The solvent was removed at the end of the reaction to obtain the crude product, which was separated on a flash column to yield the product as a white solid (470 mg).

Example 3

Biodegradable Crosslinker

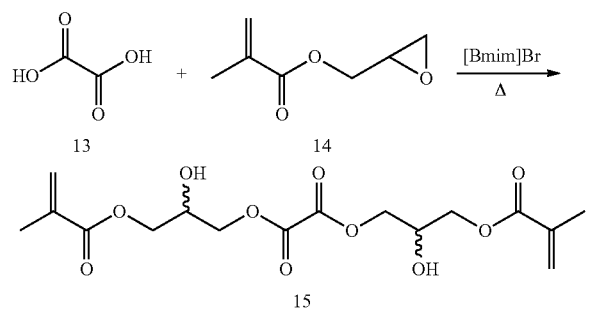

Synthesis of oxalate diester crosslinker, 15: To a 100 mL round bottom flask with a stir bar was added oxalic acid (13, 5.4 g, 60 mmol), 1-butyl-3-methylimidazolium bromide ([Bmim]Br) (18 g, 84 mmol) and 4-methoxyphenol (120 mg, 0.97 mmol). The content was melted at 90° C. with stirring for 15 minutes. After adding glycidyl methacrylate (14, 17.04 g. 120 mmol), the reaction was stirred at 90° C. for 1 hour. Thin layer chromatography stain with 4-(4-nitrobenzyl)pyridine showed full consumption of the epoxide. The reaction mixture was suspended in 200 mL of EtOAc and washed with water (100 mL×2), saturated sodium bicarbonate (100 mL×2), and brine (100 mL). The organic phase was collected and dried over sodium sulfate. The crude was dried under vacuum and purified with flash chromatography (DCM/EtOAc). Total of 12.7 g of purified product was obtained as a clear liquid.

Example 4

Biodegradable Crosslinker

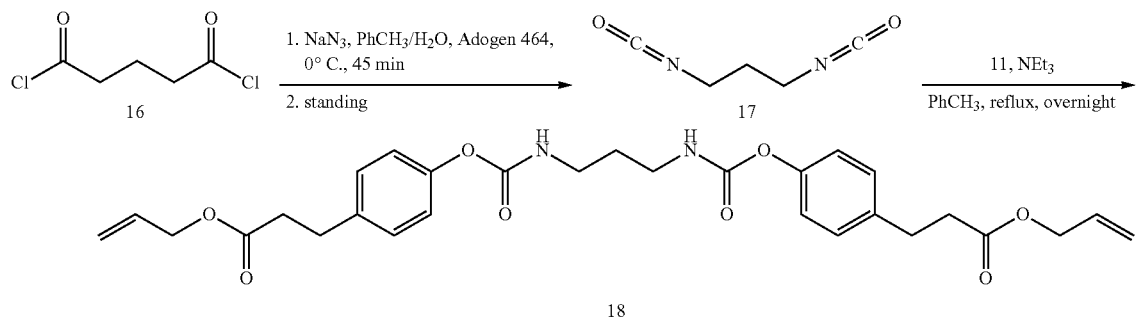

Synthesis of 1,3-diisocyanatopropane, 17: To a 500 mL three-neck round bottom flask fitted with a stir bar was added toluene (109 mL) and glutaryl dichloride (16, 8.6 g, 53 mmol). The flask was then cooled in an ice bath. Then Adogen 464 (52 µL) was added. In a separate Erlenmeyer flask, sodium azide (3.62 g, 55.65 mmol) was dissolved in distilled water (109 mL). The sodium azide solution was then added to the reaction mixture chilled on the ice bath. The reaction mixture was stirred at room temperature for 1.5 hours and then was poured into a 500 mL separatory funnel. The aqueous layer was drained and the toluene fraction was washed with distilled water (100 mL×1), followed by saturated NaCl solution (100 mL×1). The organic fraction was dried over anhydrous Na$_2$SO$_4$. The organic fraction was then filtered over a Buchner funnel, and the filtrate was placed on a rotary evaporator until about 80 grams of toluene was removed. The diisocyanate was kept as a solution in toluene and stored in a fridge.

Synthesis of dicarbamate crosslinker, 18: A solution consisting of about 35.1% (wt %) of the diisocyanatopropane, 17 in toluene was prepared as described above. To a 500 mL three-neck round bottom flask fitted with a stir bar, under argon was added the diisocyanatopropane solution (17, 1.2 g), allyl 3-(4-hydroxyphenyl)propionate (11, 3.93 g, 19.1 mmol), toluene (54.1 mL), and triethylamine (2.44 mL, 17.49 mmol) sequentially. The reaction was placed in an oil bath and heated to reflux. After 2 hours of reaction, an aliquot of the diisocyanatopropane solution (17, 1 g) was added to the reaction. After 2.5 hours of reaction, another aliquot of the diisocyanatopropane solution (17, 1 g) was added. The reaction was refluxed overnight. After cooling to room temperature, the reaction was washed with 5% citric acid (50 mL×1) and saturated sodium chloride (50 mL×1). The solution was dried over anhydrous Na$_2$SO$_4$ and filtered. The filtrate was concentrated on a rotary evaporator to afford the product as a white solid (4.62 g).

Example 5

Biodegradable Crosslinker

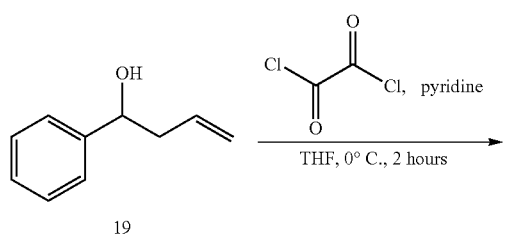

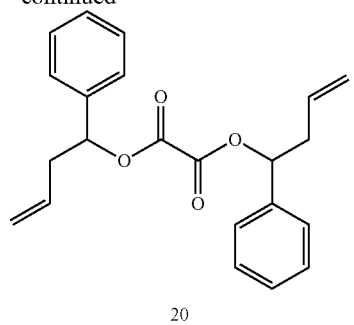

Synthesis of oxalate diester crosslinker, 20: To a 1 liter three-neck round bottom flask fitted with an addition funnel and a stir bar was added 1-phenyl-3-buten-1-ol (19, 2 g, 13.5 mmol) and tetrahydrofuran (THF) (340 mL). To this solution was added pyridine (7 mL, 86.6 mmol). The flask was then cooled on an ice bath. To the addition funnel was added THF (170 mL) and oxalyl chloride (0.58 mL, 6.57 mmol). The oxalyl chloride solution was added into the flask dropwise over 50 min. After 40 min of stirring, more oxalyl chloride (0.58 mL, 6.75 mmol) was added. The reaction was stirred for an additional 50 min, before it was pulled out of the ice bath. To work up, the precipitate was filtered off. The solution was concentrated to about 30 mL. Ethyl acetate (50 mL) was added to the flask to dissolve the residue. The ethyl acetate solution was washed with 5% citric acid solution (100 mL×1) and saturated NaHCO$_3$ solution (100 mL×1). The organic fraction was dried over MgSO$_4$. The solvent was removed on a rotary evaporator to afford the product as a yellow oil.

Example 6

Biodegradable Crosslinker

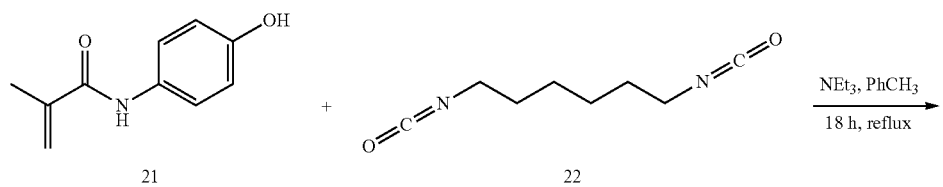

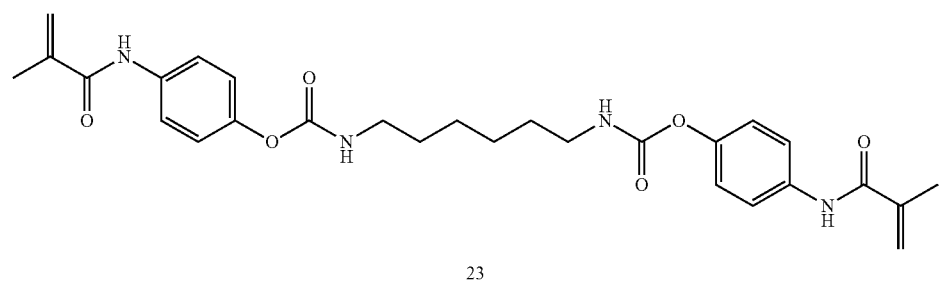

Synthesis of dicarbamate crosslinker, 23: To an oven-dried 2 L three-neck round bottom flask fitted with a stir bar and a reflux condenser, under argon was added hexamethylene diisocyanate (22, 19.1 mL, 0.119 mol), toluene (760 mL), and triethylamine (36.5 mL, 0.262 mol). Added N-(4-hydroxyphenyl)methacrylamide (21, 50.7 g, 0.286 mol) and 25.4 mg hydroquinone to the flask. Stirred vigorously and until everything dissolved. The flask was placed in a 110° C. oil bath or heating mantel and heated to reflux the reaction overnight. To work up, the toluene fraction was washed with 5% citric acid (200 mL×2) and saturated NaCl solution (200 mL×1). The toluene fraction was poured into a tared flask and the solvent was removed on a rotary evaporator. The fraction was separated on the flash chromatography to afford the final product as a white solid.

Example 7

Biodegradable Crosslinker

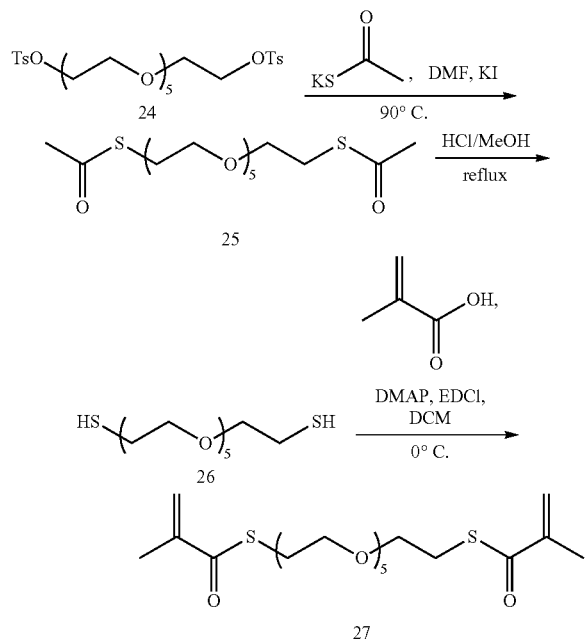

Synthesis of hexa(ethylene glycol) dithiol acetate, 25: To a 100 mL three-neck round bottom flask under argon was added anhydrous N,N-dimethylformamide (50 mL), followed by addition of hexa(ethylene glycol) di-p-toluenesulfonate (24, 6 g. 10.2 mmol), potassium thioacetate (7.25 g, 63.5 mmol) and potassium iodide (0.169 g, 1.02 mmol). The reaction was heated at 90° C. under argon for 22 hours. After the reaction was cooled down to room temperature, the crude was diluted with dichloromethane (100 mL). The resulting solution was washed with water (125 mL×5). The organic layer was dried with sodium sulfate, filtered and concentrated under vacuum. The crude was purified using flash chromatography (silica, hexane/acetone) to give 3.07 g of hexa(ethylene glycol) dithiol acetate as a clear liquid. Yield 76%, m/z 421.1 [M+Na].

Synthesis of hexa(ethylene glycol) dithiol, 26: To a 50 mL round bottom flask was added hexa(ethylene glycol) dithiol acetate (25, 3.07 g, 7.71 mmol), followed by addition of 10% hydrochloric acid (15 mL) and methanol (15 mL). The flask was connected with a condenser and the reaction mixture was heated to reflux for 3 hours. After the reaction was cooled down to room temperature, the crude was diluted with dichloromethane (50 mL). The solution was washed with water (50 mL×3) and then saturated sodium bicarbonate (50 mL×3). The organic layer was dried with sodium sulfate, filtered and concentrated under vacuum. The crude was purified using flash chromatography (silica, dichloromethane/acetone) to give 1.50 g of hexa(ethylene glycol) dithiol. Yield 62%.

Synthesis of hexa(ethylene glycol) dithiol methacrylate, 27: To a 100 mL three-neck round bottom flask under argon was added 50 mL of anhydrous dichloromethane followed by addition of hexa(ethylene glycol) dithiol (26, 1.50 g, 4.78 mmol). The reaction mixture was chilled on ice for 30 min. To the reaction mixture was added 4-dimethylaminopyridine (0.12 g, 1 mmol) and methacrylic acid (1.6 mL, 19.1 mmol). The reaction mixture was then stirred for 15 min followed by addition of 1-ethyl-3-(3-dimethylaminopropyl)carbodiimide. The reaction was continued to stir for 3 hours at 0° C. until thin layer chromatography with iodine spray indicated that the dithiol was fully consumed. The reaction mixture was extracted with saturated sodium bicarbonate (50 mL) to remove excess methacrylic acid. The aqueous layer was extracted with ethyl acetate (50 mL×2). The organic layers were combined, dried with sodium sulfate, filtered and concentrated under vacuum. The crude was reconstituted in 50 mL of ethyl acetate/dichloromethane (3:7) and passed through 10 g of silica. The silica was further washed with 100 mL of ethyl acetate/dichloromethane (3:7). The washes were combined and concentrated under vacuum. The crude was purified using flash chromatography (silica, dichloromethane/ethyl acetate) to give 1.85 g of hexa(ethylene glycol) dithiol methacrylate as a clear liquid. Yield 86%, m/z 473.2 [M+Na], $^1$H NMR (DIMETHYL SULFOXIDE-d): δ 1.915 (6H), 3.08 (4H), 3.51 (16H), 3.53 (4H), 5.75 (2H), 6.035 (2H).

Example 8

Preparation of Particles

Mineral oil (300 mL) was added to a sealed jacketed-reaction vessel equipped with an overhead stirring element and a heating element maintained at 70° C. The vessel was sparged with argon for at least 4 hours while mixing. A prepolymer solution was prepared by dissolving 1.5 g dimethylacrylamide, 1.5 g glycerol monomethacrylate, 4.6 g 3-sulfopropyl acrylate, 0.35 g of azobisisobutyronitrile and 5.5 g of a crosslinker prepared in Examples 1-7, in 25.0 g of N,N-dimethylformamide. Once dissolved, the solution was sparged with argon for 5 min. Azobisisobutyronitrile (0.40 g) was added to the reaction vessel and overhead stirring increased to 300 rpm. After approximately 10 min, an aliquot of SPAN® 80 (0.8 mL) was added to the mineral oil and allowed to mix. The prepolymer solution was added to the reaction vessel and the resulting suspension was allowed to polymerize for an hour before the heat was turned off. The resulting solution was mixed in the reaction vessel overnight.

Example 9

Purification of Particles

After the polymerization was complete, an aliquot of hexane was added to the reaction vessel and the polymer particles were washed to remove leftover mineral oil. The particles were separated from the solution, and washed with an aliquot of N,N-dimethylformamide. Washes with fresh portions of solution were repeated for hexane and N,N-dimethylformamide. The resulting mixture was washed three times with phosphate buffered saline (PBS).

The particles were separated by sizes using a sieving process. Sieves were stacked from the largest size (on top) to the smallest size (on bottom). A sieve shaker was utilized to aid in the sieving process. The particles were placed on the top sieve along with an aliquot of PBS. Once all the particles had been sorted, they were collected and placed in bottles according to their size.

After sieving, the particles were dehydrated to extend their shelf life. While mixing, the particles were placed in a graded series of acetone/water mixtures. For at least 24 hours, the particles were suspended in solvent mixtures ranging from 75% to 100% acetone. Subsequently, the particles were lyophilized, packaged, and sterilized.

Example 10

Degradation of Particles

Samples of particles prepared with differing monomers, crosslinkers and reagent concentrations were placed in PBS and stored at 37° C. to determine degradation time. The visual analysis included color and transparency of the particles, ability to see the particle outline, and the number of particles visible. The grading scale for the samples included (5) no change in particle numbers, outlines, or quantity from the beginning of the experiment, (3) faint particle outline with a good number of particles still visible, (1) very few particles visible, and (0) no particles observed in sample. Results for the comparison of different crosslinking agents are illustrated in FIG. 1. The results illustrate that degradation rate can be dependent on the structure of the crosslinker used.

Figure 2:
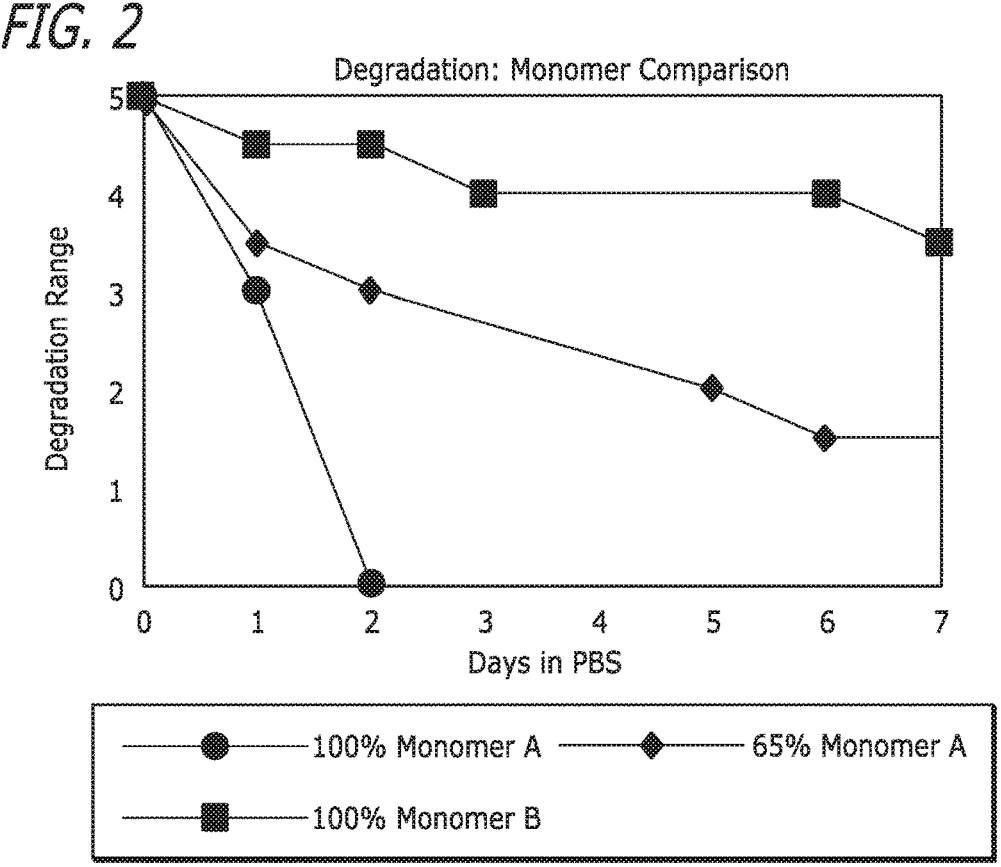
FIG. 2 illustrates graphically, particle degradation time at 37° C. as a function of two different types of monomers with the same crosslinker and concentration.

FIG. 2 graphically shows degradation time at 37° C. as a function of two different types of monomers with the same crosslinker and concentration. As illustrated, degradation can be dependent on the type of monomers used. Selection of the monomer(s) and crosslinker(s) used are two properties that can be varied to tailor degradation time as needed.

Figure 3:
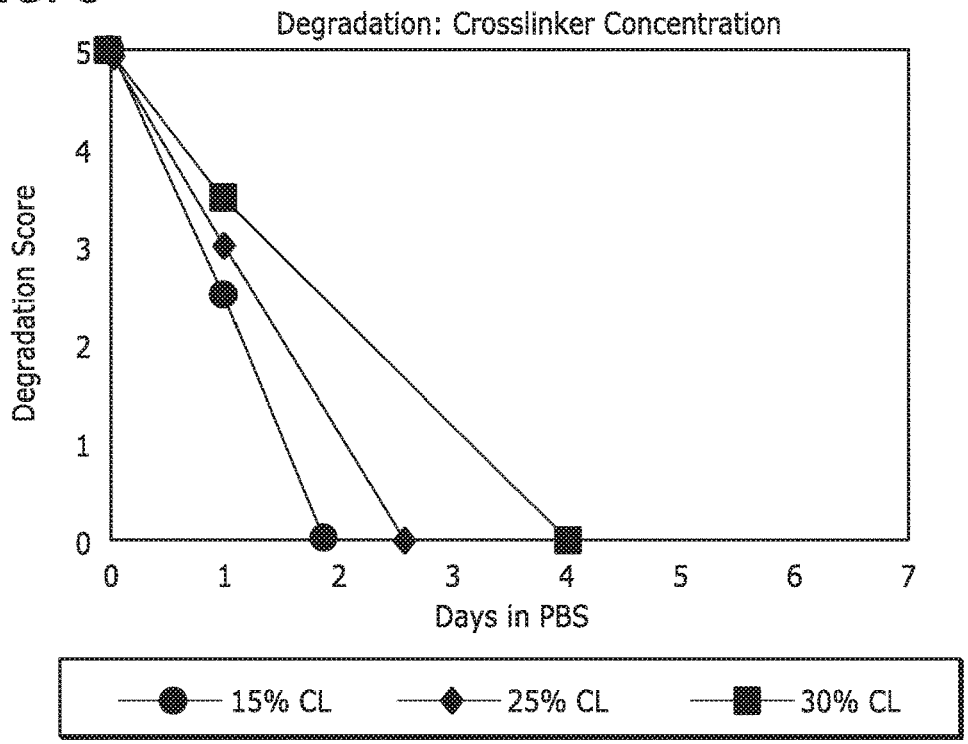
FIG. 3 illustrates graphically, particle degradation time at 37° C. as a function of the amount of crosslinker.

FIG. 3 graphically shows degradation time at 37° C. as a function of the amount of crosslinker. As illustrated, the greater the percentage of crosslinker the slower the degradation rate. This feature can also be varied to tailor degradation time as needed.

Example 11

In Vitro Elution of Pharmaceutical Agents from Particles

Figure 4:
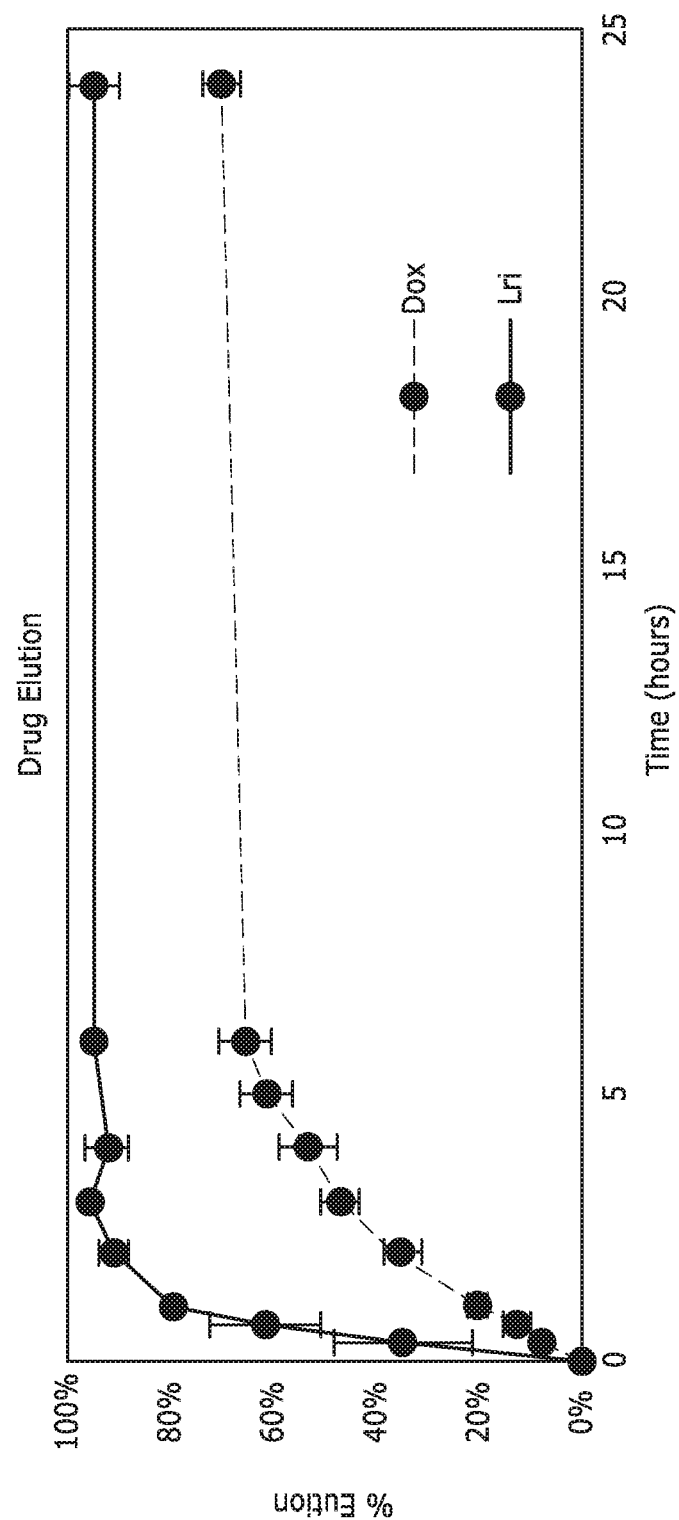
FIG. 4 illustrates high performance liquid chromatography results from Example 11.

For in vitro elution testing, drug was loaded on 1 mL samples of microspheres of approximately 400±100 micron diameter. Microsphere aliquots were loaded with 37.5 mg of doxorubicin in water or 50 mg of irinotecan in citrate buffer. Samples were incubated for 18 hours. Drug was eluted from the samples in a Sotax USP 4 dissolution apparatus. Samples were taken at incremental time intervals and analyzed by high performance liquid chromatography. Peak area was recorded (FIG. 4). Percent and concentration of drug eluted were calculated for each time interval. A 1 mL microsphere sample loaded with 37.5 mg doxorubicin eluted 24.5 mg (65%) over the first day; and, a sample loaded with 50 mg irinotecan eluted over 45 mg (95%) over the first day.

Example 12

In Vivo Elution of Pharmaceutical Agents from Particles

Figure 5:
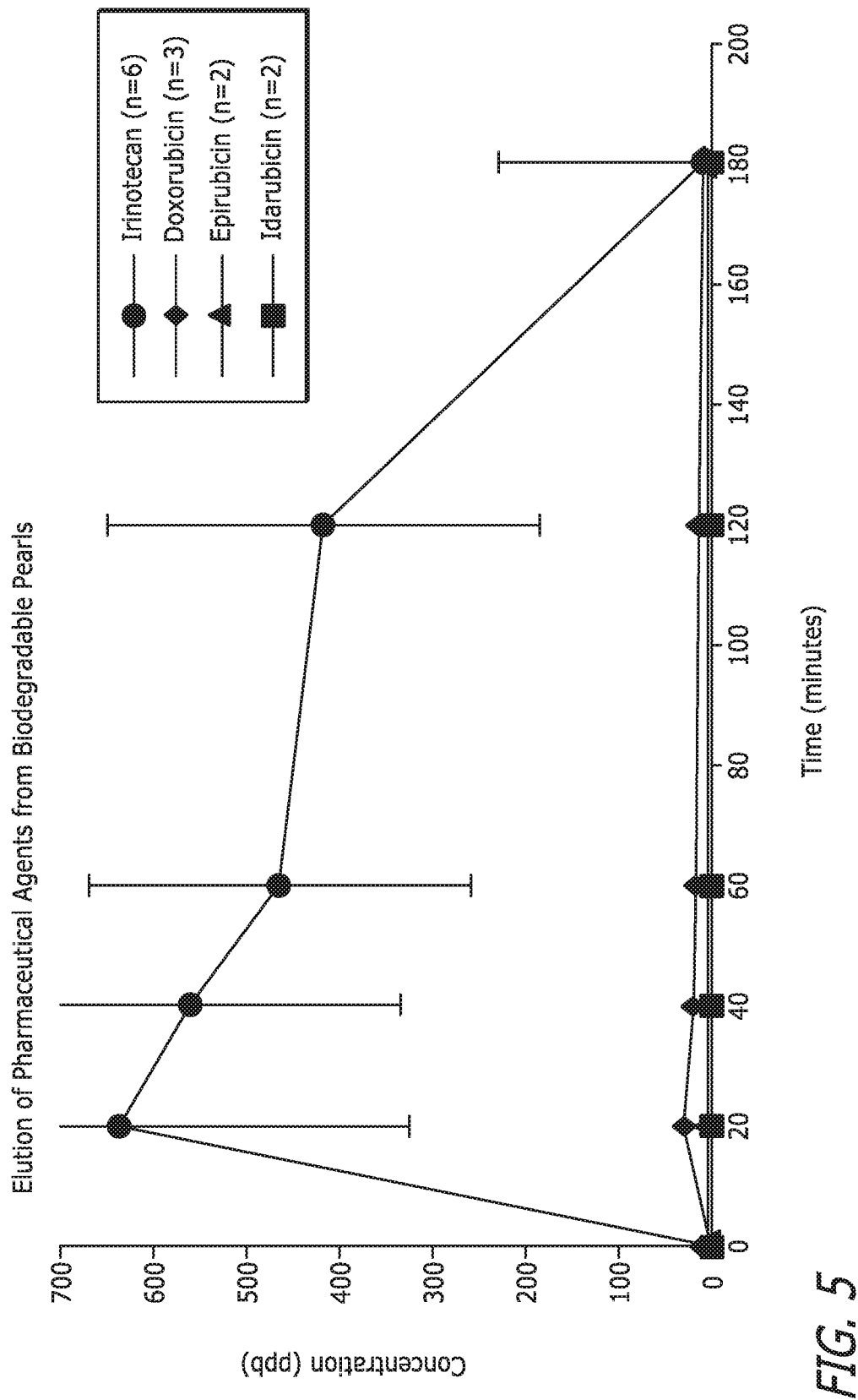
FIGS. 5 and 6 illustrate systemic concentration of pharmaceutical agent elution in plasma overtime.
Figure 6:
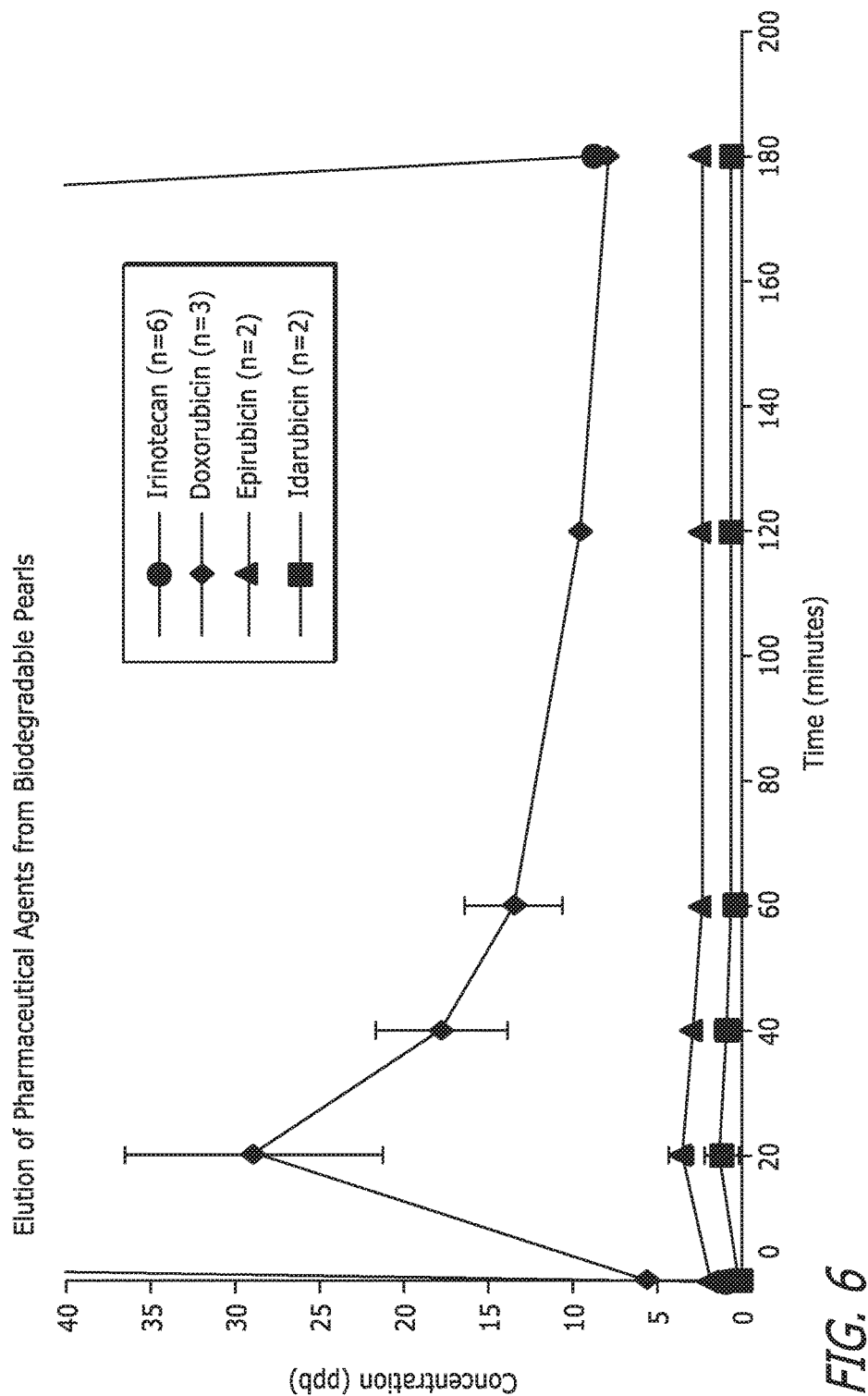

Blood samples were obtained to determine the systemic concentration of pharmaceutical agent before embolization as well as 20, 40, 60, 120 and 180 minutes post-embolization. Plasma was prepared by centrifugation and the samples were frozen at −80° C. until analysis. Quantitation was done via liquid chromatography-tandem mass spectrometry (LC/MS/MS) using an Agilent 1260 Infinity HPLC system coupled with ABSciex 4000 Q Trap LC/MS/MS system. Chromatographic separation was performed using an Agilent Poroshell 120 C18 column (4.6 mm×50 mm, 2.7 µm) at 25° C. and mobile phases consisting of A: 0.1% formic acid in acetonitrile and B: 0.1% formic acid in water. The plasma samples were precipitated with 3 fold excess (v/v) of acetonitrile containing 50 ppb of an internal standard. After being vortexed and centrifuged at 13,000 rpm at 4° C. for 10 minutes, the supernatant of each sample was diluted with 0.1% formic acid in water. Injection of 20 µL of the diluted sample was performed. The calibration curve was prepared by spiking blank plasma over the analytical range for each agent. The systemic concentration of each agent in plasma overtime is shown in FIGS. 5 and 6.

Example 13

Preparation of Particles

Mineral oil (500 mL) was added to a sealed jacketed-reaction vessel equipped with an overhead stirring element and a heating element maintained at 74° C. The vessel was sparged with argon for at least 4 hours while mixing. A prepolymer solution was prepared by dissolving 0.5 g dimethylacrylamide, 2.75 g glycerol monomethacrylate, 4.9 g 3-sulfopropyl acrylate, 0.35 g of azobisisobutyronitrile and 5.25 g of a crosslinker prepared in Examples 1-7, in 25.0 g of dimethyl sulfoxide. Once dissolved, the solution was sparged with argon for 5 min. If desired, an aliquot of Triton® X-100 (0.2 mL) can be added to the formulation and allowed to mix. Azobisisobutyronitrile (0.50 g) was added to the reaction vessel and overhead stirring increased to 325 rpm. After approximately 2 min, an aliquot of SPAN® 80 (2.5 mL) was added to the mineral oil and allowed to mix. The prepolymer solution was added to the reaction vessel and the resulting suspension was allowed to polymerize for an hour before the heat was turned off. The resulting solution was mixed in the reaction vessel overnight.

Example 14

Washing of Particles

After the polymerization was complete, an aliquot of hexane was added to the reaction vessel and the polymer particles were washed to remove leftover mineral oil. The particles were separated from the solution, and washes with fresh portions of solution were repeated. The particles were once again separated from solution, and washed with an aliquot of isopropyl alcohol. After decanting off the solution, the particles were washed with a mixture of isopropyl alcohol and phosphate buffered saline (PBS). The resulting mixture was washed three times with 70% isopropyl alcohol.

The particles were separated by sizes using a sieving process. Sieves were stacked from the largest size (on top) to the smallest size (on bottom). A sieve shaker was utilized to aid in the sieving process. The particles were placed on the top sieve along with an aliquot of 70% isopropyl alcohol. Once all the particles had been sorted, they were collected and placed in bottles according to their size.

After sieving, the particles were dehydrated to extend their shelf life. While mixing, the particles were placed in a graded series of acetone/water mixtures. For at least 24 hours, the particles were suspended in solvent mixtures ranging from 75% to 100% acetone. Subsequently, the particles were lyophilized, packaged, and sterilized.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Embodiments of this invention are described herein, including the best mode known to the inventors for carrying out the invention. Of course, variations on those embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. An embolic system including:
a syringe, a vial, or a combination thereof; and
polymer particles comprising at least one monomer including at least one functional group and at least one crosslinker having a structure

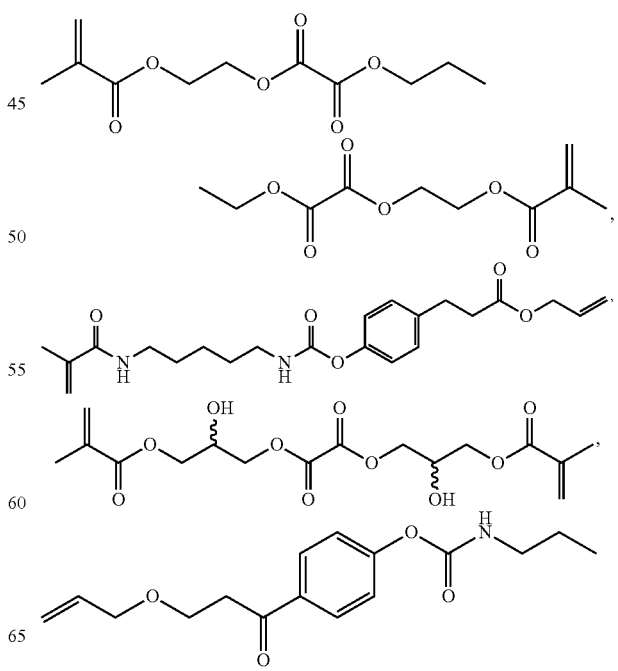

-continued

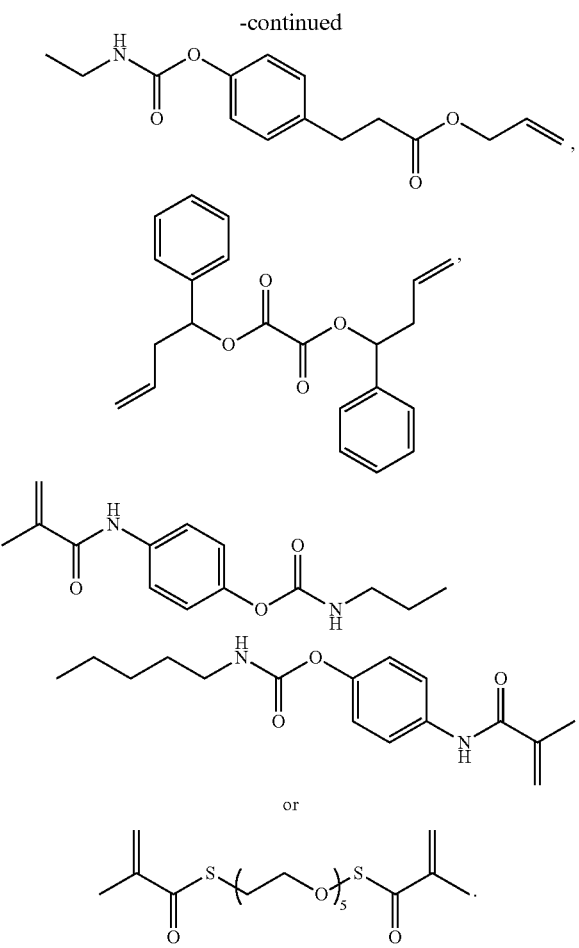

2. The embolic system of claim 1, wherein the polymer particles have a diameter between about 40 μm and about 1,200 μm.

3. The embolic system of claim 1, wherein the polymer particles have a diameter between about 75 μm and about 1,200 μm.

4. The embolic system of claim 1, wherein the at least one functional group is acrylate, acrylamide, methacrylate, or methacrylamide.

5. The embolic system of claim 1, wherein the at least one monomer includes an ionizable functional group.

6. The embolic system of claim 5, wherein the ionizable functional group is basic.

7. The embolic system of claim 5, wherein the ionizable functional group is acidic.

8. The embolic system of claim 1, wherein the polymer particles include a second crosslinker including a second linkage selected from an ester, a thioester, a carbonate, a peptide cleavable by matrix metalloproteinases, a peptide cleavable by matrix collagenases, a peptide cleavable by matrix elastases, and a peptide cleavable by matrix cathepsins.

9. The embolic system of claim 1, wherein the polymer particles are biodegradable.

10. The embolic system of claim 1, wherein the polymer particles are substantially degraded within about 1 months of implantation.

11. The embolic system of claim 1, wherein the at least one monomer is dimethylacrylamide.

12. The embolic system of claim 1, wherein the at least one monomer is acrylamide.

13. A method of treatment, the method comprising:
delivering a solution including polymer particles through a delivery device to a treatment site,
wherein the polymer particles include at least one monomer including at least one functional group and at least one crosslinker having a structure

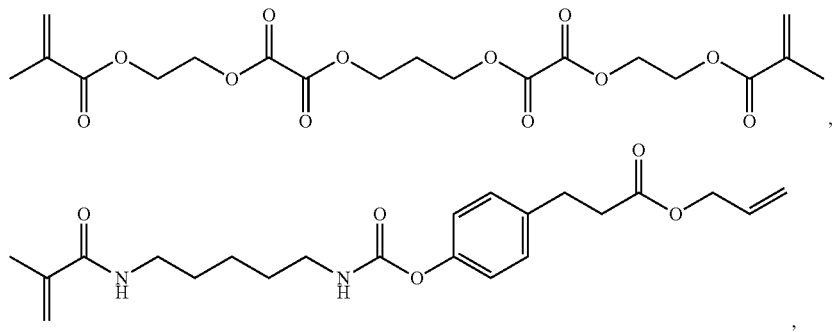

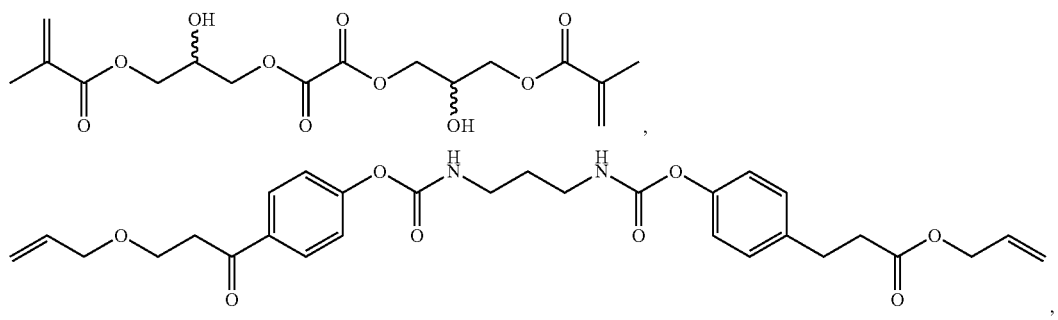

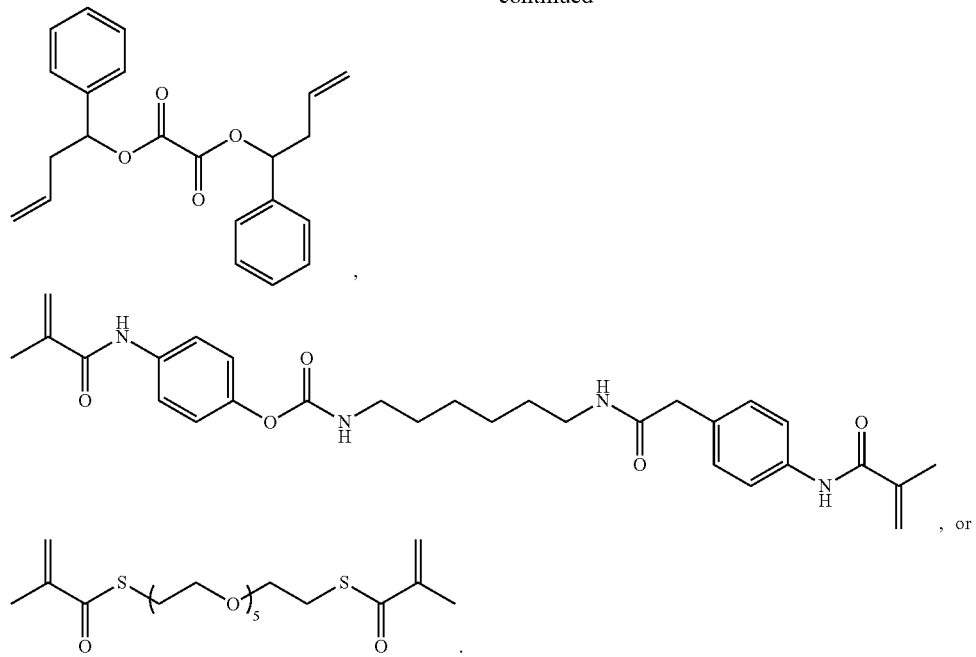

14. The method of claim 13, wherein the polymer particles have a diameter between about 40 μm and about 1,200 μm.

15. The method of claim 13, further comprising:
mixing a radiopaque contrast agent with the polymer particles.

16. The method of claim 13, wherein the delivering is through a catheter, a microcatheter, or a needle.

17. The method of claim 13, further comprising:
occluding blood flow using the polymer particles.

18. The method of claim 13, wherein the polymer particles include a second crosslinker including a second linkage selected from an ester, a thioester, a carbonate, a peptide cleavable by matrix metalloproteinases, a peptide cleavable by matrix collagenases, a peptide cleavable by matrix elastases, and a peptide cleavable by matrix cathepsins.

19. The method of claim 13, wherein the polymer particles are biodegradable.

20. The method of claim 19, wherein the polymer particles are substantially degraded within about 6 months of implantation.

* * * * *